US012690771B2

(12) United States Patent
Agrawal et al.

(10) Patent No.: US 12,690,771 B2
(45) Date of Patent: Jul. 28, 2026

(54) MULTISPECTRAL PHOTOACOUSTIC DEVICES

(71) Applicant: QUALCOMM Incorporated, San Diego, CA (US)

(72) Inventors: Sumit Agrawal, Sunnyvale, CA (US); Ye Zhan, Buffalo, NY (US); Emily Kathryn Brooks, Amherst, NY (US); Hrishikesh Vijaykumar Panchawagh, Cupertino, CA (US); Ali Lopez, Dublin, CA (US); Nicholas Buchan, San Jose, CA (US); Kostadin Dimitrov Djordjev, Los Gatos, CA (US); John Keith Schneider, Williamsville, NY (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 18/461,394

(22) Filed: Sep. 5, 2023

(65) Prior Publication Data

US 2025/0072761 A1 Mar. 6, 2025

(51) Int. Cl.
*A61B 5/00* (2006.01)
*A61B 5/02* (2006.01)
*A61B 5/021* (2006.01)

(52) U.S. Cl.
CPC ........ *A61B 5/0095* (2013.01); *A61B 5/02007* (2013.01); *A61B 5/021* (2013.01)

(58) Field of Classification Search
CPC .... A61B 5/0095; A61B 5/02007; A61B 5/021
See application file for complete search history.

(56) References Cited

U.S. PATENT DOCUMENTS

| | | | |
|---|---|---|---|
| 7,015,983 B2 | 3/2006 | Saccomanno | |
| 2007/0093717 A1* | 4/2007 | Nagar | A61B 5/489 |
| | | | 600/438 |

(Continued)

FOREIGN PATENT DOCUMENTS

| | | |
|---|---|---|
| CN | 115517628 A | 12/2022 |
| EP | 2684524 B1 | 1/2017 |

(Continued)

OTHER PUBLICATIONS

International Search Report and Written Opinion—PCT/US2024/045172—ISA/EPO—Nov. 19, 2024.

*Primary Examiner* — Bo Joseph Peng
(74) *Attorney, Agent, or Firm* — Weaver Austin Villeneuve & Sampson LLP

(57) ABSTRACT

An apparatus may include a platen, a light source system, an ultrasonic receiver system and a control system, the light source system configured for providing first light of a first wavelength and second light of a second wavelength to a target object on an outer surface of the platen. The control system may be configured to: cause the light source system to provide the first light to the target object at a first time and to provide the second light to the target object at a second time; receive first ultrasonic receiver signals and second ultrasonic receiver signals from the ultrasonic receiver system corresponding to photoacoustic responses of the target object to the first light and the second light, respectively; and estimate one or more blood vessel features based on at least one of the first ultrasonic receiver signals or the second ultrasonic receiver signals.

16 Claims, 19 Drawing Sheets

(56) References Cited

U.S. PATENT DOCUMENTS

| | | | |
|---|---|---|---|
| 2010/0229650 A1 | 9/2010 | Shahzad et al. | |
| 2010/0268058 A1* | 10/2010 | Chen | A61B 8/4483 |
| | | | 600/407 |
| 2013/0137959 A1 | 5/2013 | Lisogurski et al. | |
| 2013/0137960 A1 | 5/2013 | Lisogurski et al. | |
| 2013/0190589 A1 | 7/2013 | Chen et al. | |
| 2014/0163353 A1* | 6/2014 | Razansky | A61B 5/0095 |
| | | | 600/407 |
| 2015/0133765 A1 | 5/2015 | Ichihara et al. | |
| 2015/0241393 A1 | 8/2015 | Ganti et al. | |
| 2016/0081557 A1* | 3/2016 | Lee | G01N 29/2418 |
| | | | 600/407 |
| 2016/0150973 A1* | 6/2016 | Abe | A61B 5/062 |
| | | | 600/407 |
| 2016/0213257 A1* | 7/2016 | Nishihara | A61B 5/0095 |
| 2017/0231598 A1 | 8/2017 | Baek et al. | |
| 2017/0323131 A1 | 11/2017 | Lu et al. | |
| 2017/0323132 A1 | 11/2017 | Lu et al. | |
| 2017/0332914 A1 | 11/2017 | Chapman et al. | |
| 2019/0150757 A1 | 5/2019 | Suehira | |
| 2019/0239860 A1* | 8/2019 | Hayashi | A61B 8/463 |
| 2019/0377962 A1 | 12/2019 | Kitchens et al. | |
| 2020/0302140 A1 | 9/2020 | Lu et al. | |
| 2020/0410190 A1 | 12/2020 | Kitchens et al. | |
| 2021/0052164 A1* | 2/2021 | Shnaiderman | A61B 5/14542 |
| 2021/0117519 A1 | 4/2021 | Yoon et al. | |
| 2022/0022757 A1 | 1/2022 | Choi et al. | |
| 2022/0133273 A1* | 5/2022 | Dangi | A61B 5/0095 |
| | | | 600/459 |
| 2022/0175258 A1* | 6/2022 | Kitchens | A61B 5/02116 |
| 2023/0157551 A1 | 5/2023 | Nam et al. | |
| 2025/0072760 A1 | 3/2025 | Agrawal et al. | |
| 2025/0072762 A1 | 3/2025 | Agrawal et al. | |
| 2025/0072763 A1 | 3/2025 | Agrawal et al. | |

FOREIGN PATENT DOCUMENTS

| | | | |
|---|---|---|---|
| EP | 2203734 B1 | 2/2018 | |
| WO | 2019143579 A1 | 7/2019 | |

* cited by examiner

Figure 1:
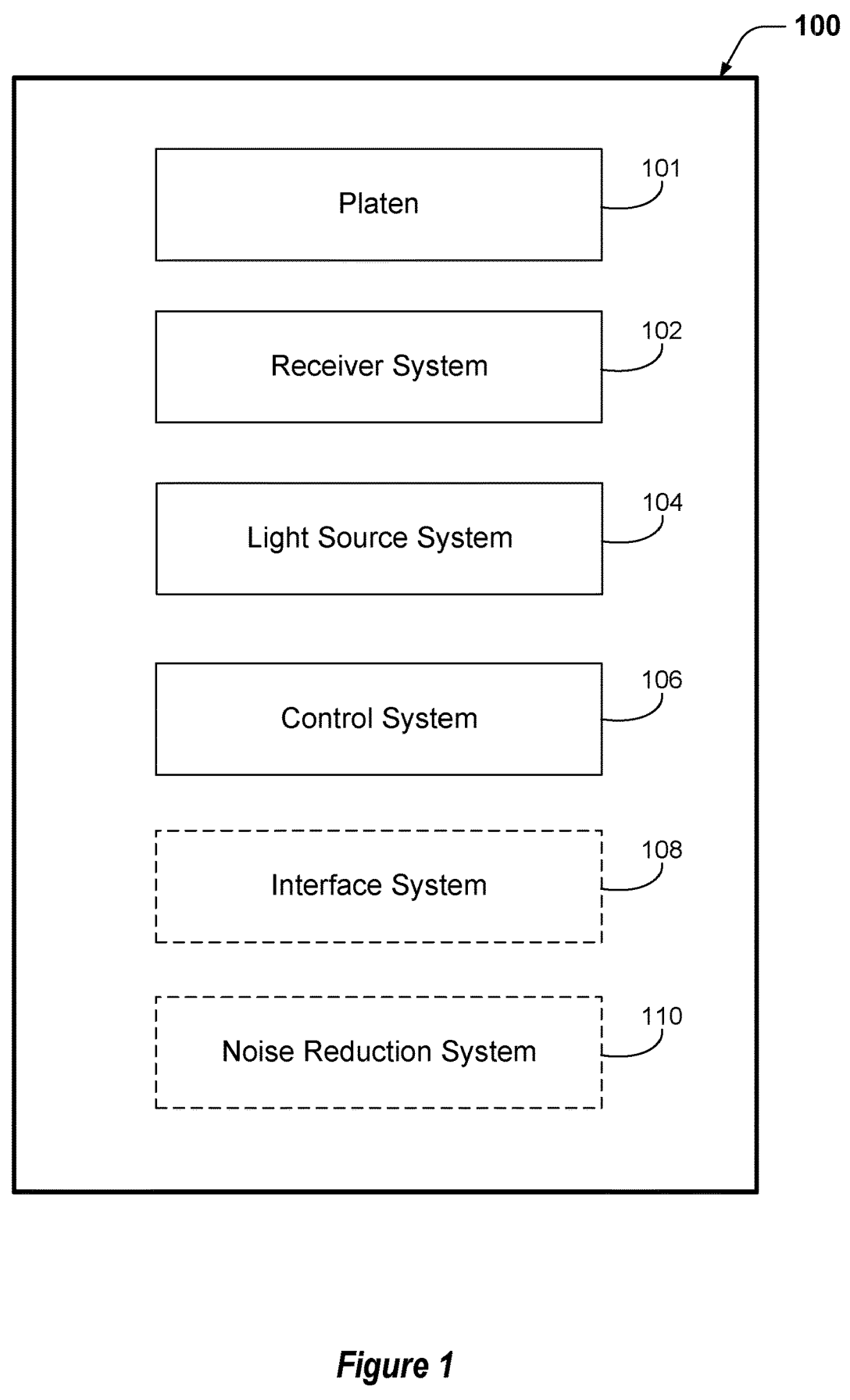

100

Platen 101

Receiver System 102

Light Source System 104

Control System 106

Interface System 108

Noise Reduction System 110

Top View of 2D
Array

102

Transparent platen
201

Array of
transparent
electrodes 820

Transparent
piezo layer
415

1035a

102

408a

Transparent platen
201

Array of
transparent
electrodes 820

Transparent
piezo layer
415

1045a

104

1035b    1045b

1100

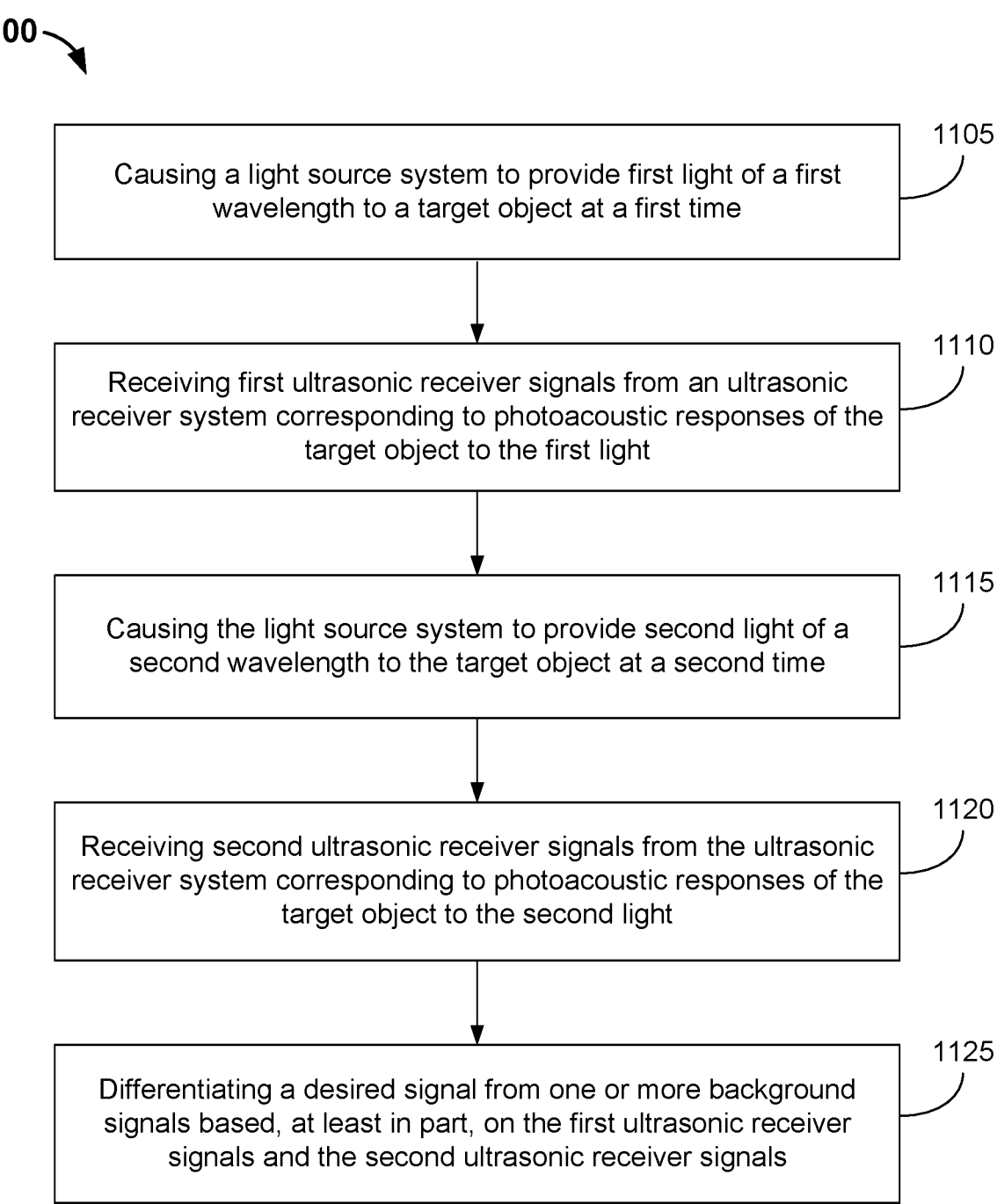

1105
Causing a light source system to provide first light of a first wavelength to a target object at a first time 1110
Receiving first ultrasonic receiver signals from an ultrasonic receiver system corresponding to photoacoustic responses of the target object to the first light 1115
Causing the light source system to provide second light of a second wavelength to the target object at a second time 1120
Receiving second ultrasonic receiver signals from the ultrasonic receiver system corresponding to photoacoustic responses of the target object to the second light 1125
Differentiating a desired signal from one or more background signals based, at least in part, on the first ultrasonic receiver signals and the second ultrasonic receiver signals

MULTISPECTRAL PHOTOACOUSTIC DEVICES

TECHNICAL FIELD

This disclosure relates generally to photoacoustic devices and systems.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and ambulatory monitoring. Some such devices are, or include, photoacoustic devices. Although some previously-deployed photoacoustic devices and systems can provide acceptable results, improved photoacoustic devices and systems would be desirable.

SUMMARY

The systems, methods and devices of this disclosure each have several aspects, no single one of which is solely responsible for the desirable attributes disclosed herein.

One innovative aspect of the subject matter described in this disclosure can be implemented in an apparatus. In some implementations, a mobile device (such as a wearable device, a cellular telephone, etc.) may be, or may include, at least part of the apparatus. The apparatus may include a platen, a light source system and a receiver system. The receiver system may be, or may include, an ultrasonic receiver system configured to receive ultrasonic waves generated by the target object responsive to the light from the light source system. According to some examples, the light source system may be configured for providing light to a target object on an outer surface of the platen. In some examples, the light may include at least first light of a first wavelength—such as light having an amplitude peak at the first wavelength—and second light of a second wavelength (such as light having an amplitude peak at the second wavelength).

In some implementations, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and differentiate a desired signal from one or more background signals based, at least in part, on the first ultrasonic receiver signals and the second ultrasonic receiver signals.

According to some implementations, the apparatus may include a platen and a light source system configured for providing light to a target object on an outer surface of the platen, the light including at least first light of a first wavelength emitted by a first light-emitting device and second light of a second wavelength emitted by a second light-emitting device. In some examples, the light source system may be configured for providing the first light to the target object along a first axis and may be configured for providing the second light to the target object along the first axis. According to some implementations, the apparatus may include an ultrasonic receiver system configured to receive ultrasonic waves generated by the target object responsive to the light from the light source system and a control system configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and estimate one or more blood vessel features based on at least one of the first ultrasonic receiver signals or the second ultrasonic receiver signals.

In some implementations, the apparatus may include a platen and a light source system configured for providing light to a target object on an outer surface of the platen, the light including at least first light of a first wavelength emitted by a first light-emitting device and second light of a second wavelength emitted by a second light-emitting device. In some examples, the light source system may include a light guide system configured to convey the first light and the second light to the platen. In some such implementations, the apparatus may include an ultrasonic receiver system configured to receive ultrasonic waves generated by the target object responsive to the light from the light source system and a control system configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and estimate one or more blood vessel features based on at least one of the first ultrasonic receiver signals or the second ultrasonic receiver signals.

According to some implementations, the apparatus may include a platen and a light source system configured for providing light to a target object on an outer surface of the platen, the light including at least first light of a first wavelength emitted by a first light-emitting device and second light of a second wavelength emitted by a second light-emitting device. In some examples, the light source system may include a light guide system including one or more light guides configured to convey light in a direction that is parallel to, or substantially parallel to, an outer surface of the platen and an ultrasonic receiver system configured to receive ultrasonic waves generated by the target object responsive to the light from the light source system. According to some such implementations, the apparatus may include a control system configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and estimate one or more blood vessel features based on at least one of the first ultrasonic receiver signals or the second ultrasonic receiver signals.

In some implementations, the light guide system may include a plurality of light extracting elements residing within the one or more light guides. The light extracting elements may be configured to direct light towards the platen. In some examples, the light extracting elements may include one or more indentations in, protuberances of, or structures formed on, a light guide surface. According to some examples, the light extracting elements may include one or more three-dimensional shapes formed from the indentations in, protuberances of, or structures formed on, the light guide surface. In some examples, the light extracting elements may include one or more beam splitters. According to some examples, the light extracting elements may include one or more mirrors or other reflective structures. In some examples, a two-dimensional array of light-extracting elements may be configured to provide substantially uniform light to an illuminated area of an outer surface of the platen. According to some examples, at least some light-extracting elements may be arranged with unequal spacing within the one or more light guides. In some such examples, light-extracting elements located farther from the first light-emitting device may be spaced closer together than light-extracting elements located closer to the first light-emitting device.

In some examples, the desired signal may correspond to a blood vessel within the target object. According to some examples, the control system may be further configured to estimate one or more blood vessel features based on at least one of the first ultrasonic receiver signals or the second ultrasonic receiver signals. In some examples, the one or more blood vessel features may include blood vessel diameter, blood vessel area, blood vessel profile, blood vessel distention, volumetric flow, pulse wave velocity, blood vessel wall thickness, or combinations thereof. According to some examples, the control system may be further configured to estimate blood pressure based, at least in part, on the one or more blood vessel features.

Other innovative aspects of the subject matter described in this disclosure can be implemented in a method. In some examples, the method may involve: causing a light source system to provide first light of a first wavelength to a target object at a first time; receiving first ultrasonic receiver signals from an ultrasonic receiver system corresponding to photoacoustic responses of the target object to the first light; causing the light source system to provide second light of a second wavelength to the target object at a second time; receiving second ultrasonic receiver signals from the ultrasonic receiver system corresponding to photoacoustic responses of the target object to the second light; and differentiating a desired signal from one or more background signals based, at least in part, on the first ultrasonic receiver signals and the second ultrasonic receiver signals.

In some examples, the desired signal may correspond to a blood vessel within the target object. According to some examples, the method may involve estimating one or more blood vessel features based on at least one of the first ultrasonic receiver signals or the second ultrasonic receiver signals. In some examples, the one or more blood vessel features may include blood vessel diameter, blood vessel area, blood vessel profile, blood vessel distention, volumetric flow, pulse wave velocity, blood vessel wall thickness, or combinations thereof. According to some examples, the method may involve estimating blood pressure based, at least in part, on the one or more blood vessel features.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 1 is a block diagram that shows example components of an apparatus according to some disclosed implementations.

FIG. 11 is a flow diagram that shows examples of some disclosed operations.

Like reference numbers and designations in the various drawings indicate like elements.

DETAILED DESCRIPTION

Figure 2A:
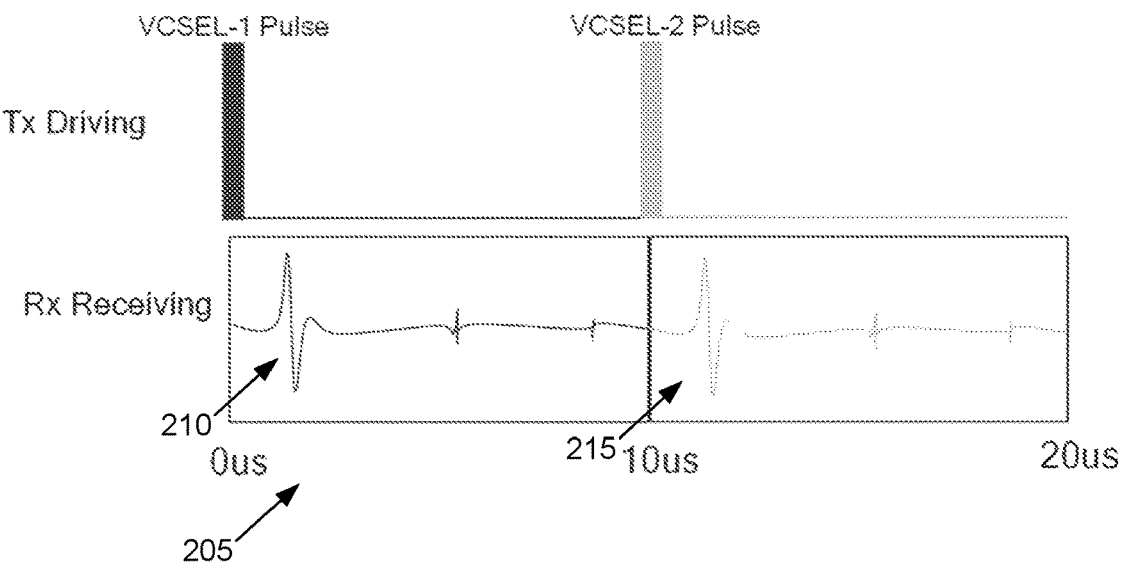
FIG. 2A shows examples of pulses emitted by a light source system and corresponding receiver signals.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Non-invasive health monitoring devices, such as photoacoustic plethysmography (PAPG)-capable devices, have various potential advantages over more invasive health monitoring devices such as cuff-capable or catheter-based blood pressure measurement devices. However, it has proven to be difficult to design satisfactory PAPG-capable devices. For example, some PAPG-capable devices that have recently been developed by the present assignee have been capable of providing light of only a single peak wavelength.

Some disclosed devices include a platen, a light source system, a receiver system and a control system. The receiver system may be, or may include, an ultrasonic receiver system. According to some examples, the light source system may be configured for providing light to a target object on an outer surface of the platen. In some examples, the light may include at least first light of a first wavelength—such as light having an amplitude peak at the first wavelength—and second light of a second wavelength (such as light having an amplitude peak at the second wavelength). Such devices are examples of what may be referred to herein as multispectral photoacoustic devices.

According to some examples, the control system may be configured to cause the light source system to provide first light of a first wavelength to a target object at a first time and to receive first ultrasonic receiver signals from an ultrasonic receiver system corresponding to photoacoustic responses of the target object to the first light. In some examples, the control system may be configured to cause the light source system to provide second light of a second wavelength to the target object at a second time, to receive second ultrasonic receiver signals from the ultrasonic receiver system corresponding to photoacoustic responses of the target object to the second light and to differentiate a desired signal from one or more background signals based, at least in part, on the first ultrasonic receiver signals and the second ultrasonic receiver signals. The desired signal may, in some instances, correspond to at least a portion of a blood vessel within the target object. According to some examples, the light source system may be configured for providing the first light and the second light to the target object along the same axis.

Particular implementations of the subject matter described in this disclosure can be implemented to realize one or more of the following potential advantages. Various disclosed configurations are multispectral photoacoustic devices capable of differentiating a desired signal from one or more background signals based, at least in part, on ultrasonic receiver signals corresponding to photoacoustic responses of a target object to light of two or more peak frequencies. In some disclosed examples, multispectral photoacoustic devices may be capable of providing enhanced optical contrast for a desired signal. At least some disclosed devices are PAPG-capable devices. In some such examples, the desired signal may correspond to at least a portion of a blood vessel. Enhanced differentiation of a blood vessel signals from background signals can provide more accurate blood pressure estimations. However, some other disclosed multispectral photoacoustic devices may be capable of providing other functionality, such as blood oxygen estimation, blood glucose estimation, chemical sensing for industrial applications, etc. Some relevant examples of the context of such implementations are described in Gliere, Alain, et al., "Challenges in the design and fabrication of a lab-on-a-chip photoacoustic gas sensor" in Sensors 14, no. 1 (2014): 957-974 and Horvath, Thomas D., et al., "Ratiometric photoacoustic sensing of pH using a "sonophore" in Analyst 133, no. 6 (2008): 747-749, both of which are hereby incorporated by reference.

FIG. 1 is a block diagram that shows example components of an apparatus according to some disclosed implementations. In this example, the apparatus 100 includes a platen 101, a receiver system 102, a light source system 104 and a control system 106. Some implementations of the apparatus 100 may include an interface system 108, a noise reduction system 110, or both.

Various examples of platens 101, light source systems 104 and receiver systems 102 are disclosed herein. Some examples are described in more detail below.

The platen 101 may be made of any suitable material, such as glass, acrylic, polycarbonate, etc. According to some examples, the platen 101 (or another portion of the apparatus) may include one or more anti-reflective layers. In some examples, one or more anti-reflective layers may reside on, or proximate, one or more outer surfaces of the platen 101.

In some examples, at least a portion of the outer surface of the platen 101 may have an acoustic impedance that is configured to approximate an acoustic impedance of human skin. The portion of the outer surface of the platen 101 may, for example, be a portion that is configured to receive a target object, such as a human digit. (As used herein, the terms "finger" and "digit" may be used interchangeably, such that a thumb is one example of a finger.) A typical range of acoustic impedances for human skin is 1.53-1.680 MRayls. In some examples, at least an outer surface of the platen 101 may have an acoustic impedance that is in the range of 1.4-1.8 MRayls, or in the range of 1.5-1.7 MRayls. Alternatively, or additionally, in some examples at least an outer surface of the platen 101 may be configured to conform to a surface of human skin. In some such examples, at least an outer surface of the platen 101 may have material properties like those of putty or chewing gum.

In some examples, at least a portion of the platen 101 may have an acoustic impedance that is configured to approximate an acoustic impedance of one or more receiver elements of the receiver system 102. According to some examples, a layer residing between the platen 101 and one or more receiver elements may have an acoustic impedance that is configured to approximate an acoustic impedance of the one or more receiver elements. Alternatively, or additionally, in some examples a layer residing between the platen 101 and one or more receiver elements may have an acoustic impedance that is in an acoustic impedance range between an acoustic impedance of the platen and an acoustic impedance of the one or more receiver elements.

In some examples, the light source system 104 may be configured to emit light through a first area of the platen 101 towards a target object in contact with the first area of the platen 101. According to some examples, the light source system 104 may include at least a first light-emitting element that is configured to emit first light of a first wavelength—such as light having an amplitude peak at the first wavelength—and a second light-emitting element that is configured to emit second light of a second wavelength (such as light having an amplitude peak at the second wavelength). In some examples, the light source system 104 may be configured to emit light at more than two wavelengths. The light may, in some implementations, be laser light.

According to some examples, the light source system 104 may be configured for providing the first light and the second light to the target object along the same axis, which may be referred to herein as a first axis. In some such examples, the receiver system 102 may receive ultrasonic receiver signals from the target object along a second axis that is different from—for example, not parallel to—the first axis. According to some examples, the second axis may be separated from the first axis by an angle in the range from 10 degrees to 60 degrees. However, in some alternative implementations, the receiver system 102 may receive ultrasonic receiver signals from the target object along a second axis that is parallel to, or substantially parallel to, the first axis. In this context, "substantially parallel" may mean within plus or minus 5 degrees, within plus or minus 10 degrees, within plus or minus 15 degrees, within plus or minus 20 degrees, etc.

In some examples, the light source system 104 may include a light guide system having one or more light guide components. The light guide system may be configured to convey light from the light source system to the platen. In some examples, the light guide component(s) may include one or more optical fibers. According to some examples, a first light guide component may be configured to transmit light from the first light-emitting component to the first area of the platen, or to another light guide component. In some examples, a second light guide component may be configured to transmit light from the second light-emitting component to the first area of the platen, or to another light guide component.

According to some examples, a light guide component may be configured to convey light in a direction that is parallel to, or substantially parallel to, the platen. In this context, "substantially parallel" may mean within plus or minus 5 degrees, within plus or minus 10 degrees, etc. In some such examples, the light guide component may include light-extracting elements, such as beam splitters, which are configured to direct light from the light guide component towards the platen.

In some examples, the receiver system 102 may include at least two receiver stack portions: a first receiver stack portion may reside proximate a first side of a first portion of the first light guide component and a second receiver stack portion may reside proximate a second side of the first portion of the first light guide component. The first receiver stack portion and the second receiver stack portion may, in some examples, be portions of a first receiver stack ring. The receiver stack ring may be configured to surround a portion of a light guide component. In some examples, the receiver system 102 may be configured to detect acoustic waves corresponding to a photoacoustic response of the target object to light emitted by the light source system.

Various examples of receiver systems 102 are disclosed herein, some of which may include ultrasonic receiver systems, optical receiver systems, or combinations thereof. In some implementations in which receiver systems 102 is, or includes, an ultrasonic receiver system, the ultrasonic receiver and an ultrasonic transmitter may be combined in an ultrasonic transceiver. In some examples, the receiver system 102 may include a piezoelectric receiver layer, such as a layer of polyvinylidene difluoride (PVDF) polymer, polyvinylidene fluoride-trifluoroethylene (PVDF-TrFE) copolymer, a piezoelectric composite, etc. In some implementations, a single piezoelectric layer may serve as an ultrasonic receiver. In some implementations, other piezoelectric materials may be used in the piezoelectric layer, such as aluminum nitride (AlN) or lead zirconate titanate (PZT). The receiver system 102 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the receiver system 102 may be, or may include, an ultrasonic receiver array. In some examples, the apparatus 100 may include one or more separate ultrasonic transmitter elements. In some such examples, the ultrasonic transmitter(s) may include an ultrasonic plane-wave generator.

The light source system 104 may, in some examples, include one or more light-emitting diodes. In some implementations, the light source system 104 may include one or more laser diodes. According to some implementations, the light source system 104 may include one or more vertical-cavity surface-emitting lasers (VCSELs). In some implementations, the light source system 104 may include one or more edge-emitting lasers. In some implementations, the light source system may include one or more neodymium-doped yttrium aluminum garnet (Nd:YAG) lasers.

The light source system 104 may, in some examples, be configured to transmit light in one or more wavelength ranges. In some examples, the light source system 104 may configured for transmitting light in a wavelength range of 500 to 600 nanometers. According to some examples, the light source system 104 may configured for transmitting light in a wavelength range of 800 to 950 nanometers.

The light source system 104 may include various types of drive circuitry, depending on the particular implementation. In some disclosed implementations, the light source system 104 may include at least one multi-junction laser diode, which may produce less noise than single-junction laser diodes. In some examples, the light source system 104 may include a drive circuit (also referred to herein as drive circuitry) configured to cause the light source system to emit pulses of light at pulse widths in a range from 3 nanoseconds to 1000 nanoseconds. According to some examples, the light source system 104 may include a drive circuit configured to cause the light source system to emit pulses of light at pulse repetition frequencies in a range from 1 kilohertz to 100 kilohertz.

In some implementations, the apparatus (for example, the receiver system 102, the light source system 104, or both) may include one or more sound-absorbing layers, acoustic isolation material, light-absorbing material, light-reflecting material, or combinations thereof. In some examples, acoustic isolation material may reside between the light source system 104 and at least a portion of the receiver system 102. In some examples, the apparatus (for example, the receiver system 102, the light source system 104, or both) may include one or more electromagnetically shielded transmission wires. In some such examples, the one or more electromagnetically shielded transmission wires may be configured to reduce electromagnetic interference from the light source system 104 that is received by the receiver system 102.

In some implementations, the light source system 104 may be configured for emitting various wavelengths of light, which may be selectable to trigger acoustic wave emissions primarily from a particular type of material. For example, because the hemoglobin in blood absorbs near-infrared light very strongly, in some implementations the light source system 104 may be configured for emitting one or more wavelengths of light in the near-infrared range, in order to trigger acoustic wave emissions from hemoglobin. However, in some examples the control system 106 may control the wavelength(s) of light emitted by the light source system 104 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the receiver system 102. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light source system 104 may be configured for emitting a light pulse with a pulse width less than about 100 nanoseconds. In some implementations, the light pulse may have a pulse width between about 10 nanoseconds and about 500 nanoseconds or more. According to some examples, the light source system may be configured for emitting a plurality of light pulses at a pulse repetition frequency between 10 Hz and 100 kHz. Alternatively, or additionally, in some implementations the light source system 104 may be configured for emitting a plurality of light pulses at a pulse repetition frequency between about 1 MHz and about 100 MHz. Alternatively, or additionally, in some implementations the light source system 104 may be configured for emitting a plurality of light pulses at a pulse repetition frequency between about 10 Hz and about 1 MHz. In some examples, the pulse repetition frequency of the light pulses may correspond to an acoustic resonant frequency of the ultrasonic receiver and the substrate. For example, a set of four or more light pulses may be emitted from the light source system 104 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 104. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 106 also may include (and/or be configured for communication with) one or more memory devices, such as one or more random access memory (RAM) devices, read-only memory (ROM) devices, etc. Accordingly, the apparatus 100 may have a memory system that includes one or more memory devices, though the memory system is not shown in FIG. 1. The control system 106 may be configured for receiving and processing data from the receiver system 102, e.g., as described below. If the apparatus 100 includes an ultrasonic transmitter, the control system 106 may be configured for controlling the ultrasonic transmitter. In some implementations, functionality of the control system 106 may be partitioned between one or more controllers or processors, such as a dedicated sensor controller and an applications processor of a mobile device.

In some examples, the control system 106 may be configured to control the light source system 104. For example, the control system 106 may be configured to control one or more light-emitting portions of the light source system 104 to emit laser pulses. The laser pulses may, in some examples, be in a wavelength range of 600 nm to 1000 nm. The laser pulses may, in some examples, have pulse widths in a range from 3 nanoseconds to 1000 nanoseconds.

According to some examples, the control system 106 may be configured to control a first light-emitting element of the light source system 104 to provide first light of a first wavelength to the target object at a first time. In some examples, the control system 106 may be configured to receive first ultrasonic receiver signals from the ultrasonic receiver system corresponding to photoacoustic responses of the target object to the first light. In some examples, the control system 106 may be configured to control a second light-emitting element of the light source system 104 to provide second light of a second wavelength to the target object at a second time. According to some examples, the control system 106 may be configured to receive second ultrasonic receiver signals from the ultrasonic receiver system corresponding to photoacoustic responses of the target object to the second light.

In some examples, the control system 106 may be configured to differentiate a desired signal from one or more background signals based, at least in part, on the first ultrasonic receiver signals and the second ultrasonic receiver signals. According to some examples, the desired signal may correspond to a blood vessel within the target object. In some examples, the control system 106 may be configured to estimate one or more blood vessel features based on the first ultrasonic receiver signals, the second ultrasonic receiver signals, or both. The one or more blood vessel features may include blood vessel diameter, blood vessel area, blood vessel profile, blood vessel distention, volumetric flow, pulse wave velocity, blood vessel wall thickness, or combinations thereof. In some examples, the control system 106 may be configured to estimate one or more cardiac features, such as blood pressure, based at least in part on the one or more blood vessel features.

According to some examples, the control system 106 may be configured to control a first light-emitting element of the light source system 104 to provide a first laser pulse of a first wavelength to the target object at a first time and to control a second light-emitting element of the light source system 104 to provide a one or more second laser pulses of a second wavelength to the target object starting at a second time. In some such examples, there may be a time interval of only a few microseconds—such as 5 nanoseconds (ns), 6 ns, 7 ns, 8 ns, 9 ns, 10 ns, 11 ns, 12 ns, 13 ns 14 ns 15 ns, etc.—between the first time and the second time. According to some such examples, the first laser pulse may cause a photoacoustic response to be emitted from the target object and also may increase the local temperature in a targeted region of the target object. In some such examples, the one or more second laser pulses also illuminate the targeted region. In some instances, because the Grüneisen parameter is temperature-dependent and because the first laser pulse causes the local temperature in the targeted region to increase, the one or more second laser pulses may produce a nonlinearly enhanced photoacoustic response from the targeted region. According to some examples, the control system 106 may be configured to receive first ultrasonic receiver signals from the ultrasonic receiver system corresponding to photoacoustic responses of the target object to the first laser pulse and to receive second ultrasonic receiver signals from the ultrasonic receiver system corresponding to photoacoustic responses of the target object to the one or more second laser pulses. In some examples, the control system 106 may be configured to control the first light-emitting element of the light source system 104 to provide one or more first laser pulses instead of a single first laser pulse.

Some implementations of the apparatus 100 may include the interface system 108. In some examples, the interface system 108 may include a wireless interface system. In some implementations, the interface system 108 may include a user interface system, one or more network interfaces, one or more interfaces between the control system 106 and a memory system and/or one or more interfaces between the control system 106 and one or more external device interfaces (e.g., ports or applications processors), or combinations thereof. According to some examples in which the interface system 108 is present and includes a user interface system, the user interface system may include a microphone system, a loudspeaker system, a haptic feedback system, a voice command system, one or more displays, or combinations thereof. According to some examples, the interface system 108 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 108 may include, a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. In some examples, the interface system 108 may include an optical sensor system, one or more cameras, or a combination thereof.

According to some examples, the apparatus 100 may include a noise reduction system 110. For example, the noise reduction system 110 may include one or more mirrors that are configured to reflect light from the light source system 104 away from the receiver system 102. In some implementations, the noise reduction system 110 may include one or more sound-absorbing layers, acoustic isolation material, light-absorbing material, light-reflecting material, or combinations thereof. In some examples, the noise reduction system 110 may include acoustic isolation material, which may reside between the light source system 104 and at least a portion of the receiver system 102, on at least a portion of the receiver system 102, or combinations thereof. In some examples, the noise reduction system 110 may include one or more electromagnetically shielded transmission wires. In some such examples, the one or more electromagnetically shielded transmission wires may be configured to reduce electromagnetic interference from circuitry of the light source system 104, receiver system circuitry, or combinations thereof, that is received by the receiver system 102.

The apparatus 100 may be used in a variety of different contexts, many examples of which are disclosed herein. For example, in some implementations a mobile device may include the apparatus 100. In some such examples, the mobile device may be a smart phone. In some implementations, a wearable device may include the apparatus 100. The wearable device may, for example, be a bracelet, an armband, a wristband, a watch, a ring, a headband or a patch.

FIG. 2A shows examples of pulses emitted by a light source system and corresponding receiver signals. In this example, a light source system has at least a first light-emitting element that is configured to emit first light of a first wavelength and a second light-emitting element that is configured to emit second light of a second wavelength. According to this example, the first light-emitting element is VCSEL-1, which is configured to emit laser light having an amplitude peak at the first wavelength. In this example, the second light-emitting element is VCSEL-2, which is configured to emit laser light having an amplitude peak at the second wavelength.

According to this example, a control system is controlling the light source system to provide the first light to a target object at a first time, which is a time interval beginning at approximately 0 microseconds (μs) in the graph 205. The graph 205 shows first ultrasonic receiver signals 210 from an ultrasonic receiver system corresponding to photoacoustic responses of the target object to the first light. In this example, the control system is controlling the light source system to provide the second light to the target object at a second time, which is a time interval beginning at approximately 10 microseconds in the graph 205. The graph 205 shows second ultrasonic receiver signals 215 from the ultrasonic receiver system corresponding to photoacoustic responses of the target object to the second light.

Figure 2B:
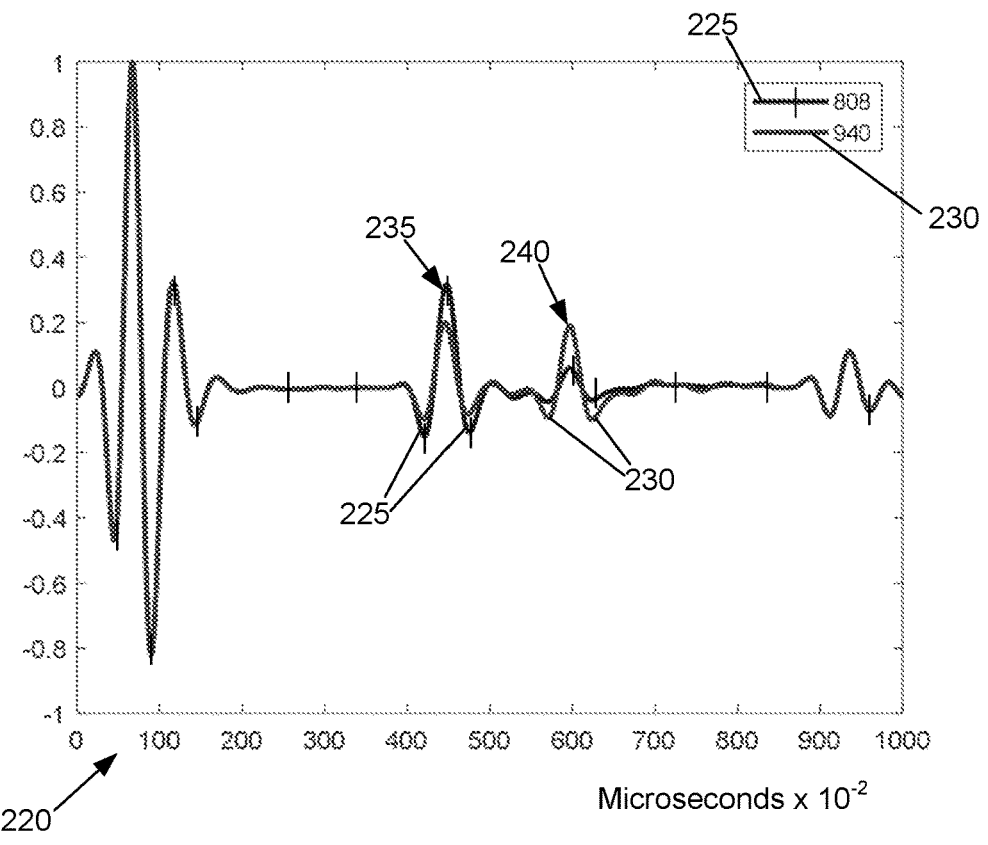
FIG. 2B shows examples of differentiating a desired signal from one or more background signals.

FIG. 2B shows examples of differentiating a desired signal from one or more background signals. The graph 220 shows ultrasonic receiver signals corresponding to photoacoustic responses of a target object, with the vertical axis indicating amplitude and the horizontal axis indicating time units in microseconds×$10^{-2}$, such that 1000 time units on graph 220 equals 10 microseconds. The curve 225 indicates ultrasonic receiver signals corresponding to photoacoustic responses of a target object to first light having a peak amplitude at a wavelength of 808 nanometers (nm) and the curve 230 indicates ultrasonic receiver signals corresponding to photoacoustic responses of a target object to second light having a peak amplitude at a wavelength of 940 nm. In these examples, the first light and the second light are both laser light.

In these examples, the peaks and troughs shown in the graph 220 during the first 200 time units correspond to electromagnetic interference (EMI). Such signals may be considered to be examples of system noise. One may observe that the curves 225 and 230 overlay one another during this time interval since the EMI does not change with the wavelength of light used for illumination.

The peaks and troughs during the time interval between approximately 400 to 660 time units correspond to the photoacoustic response of one or more skin layers and the photoacoustic response from sub-epidermal features, which in this example include blood vessel features. Signals corresponding to blood vessels are examples of what may be referred to herein as "desired signals." One may observe that the curves 225 and 230 do not overlay one another throughout this time interval. Between about 400-520 time units—for example, in the vicinity of the peak 235, which corresponds to the skin photoacoustic response—the signals corresponding to light having a peak amplitude at a wavelength of 808 nm have relatively higher amplitudes than the signals corresponding to light having a peak amplitude at a wavelength of 940 nm.. In some examples, a control system may assign a higher weight to the signals corresponding to light having a peak amplitude at a wavelength of 808 nm for imaging skin features in this time interval. In some examples, a control system may use the signals corresponding to light having a peak amplitude at a wavelength of 808 nm, and may disregard the signals corresponding to light having a peak amplitude at a wavelength of 940 nm, for imaging skin features in this time interval.

However, between about 550-650 time units—for example, in the vicinity of the peak 240, which corresponds with the front wall of an artery—the signals corresponding to light having a peak amplitude at a wavelength of 808 nm have relatively lower amplitudes than the signals corresponding to light having a peak amplitude at a wavelength of 940 nm. In some examples, a control system may assign a higher weight to the signals corresponding to light having a peak amplitude at a wavelength of 940 nm for imaging blood vessel features in this time interval. In some examples, a control system may use the signals corresponding to light having a peak amplitude at a wavelength of 940 nm, and may disregard the signals corresponding to light having a peak amplitude at a wavelength of 808 nm, for imaging blood vessel features in this time interval.

Accordingly, a multi-spectral PAPG-capable device may provide both enhanced differentiation of blood vessel signals from background signals and may provide more accurate measurements of blood vessel features such as blood vessel diameter, blood vessel area, blood vessel profile, blood vessel distention, volumetric flow, pulse wave velocity, blood vessel wall thickness, or combinations thereof. Because various methods of blood pressure estimation are based in part on measured blood vessel features, the more accurate measurements of blood vessel features provided by some disclosed multi-spectral PAPG-capable devices may also provide more accurate blood pressure estimations.

Multi-spectral photoacoustic devices can provide enhanced differentiation of desired signals from other types of background signals. For example, multi-spectral photoacoustic devices can provide enhanced differentiation of signals corresponding to skin melanosome signals, which normally have a high level of absorption at relatively shorter wavelengths of light—such as wavelengths of light in the 400-500 nm range—and lower levels of absorption at longer wavelengths of light, such as wavelengths of light in the 800-900 nm range.

Figure 2C:
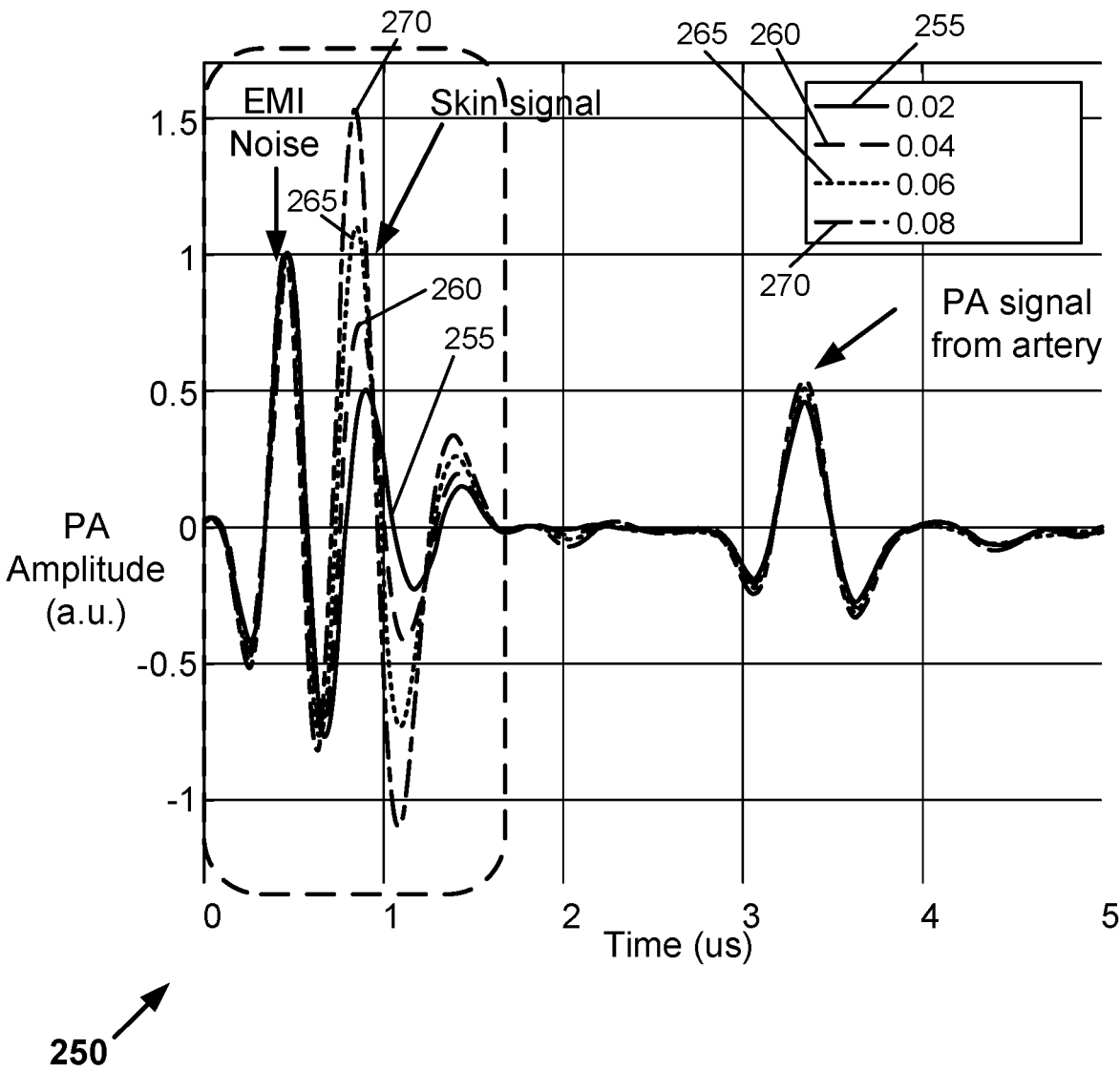
FIG. 2C shows additional examples of differentiating a desired signal from one or more background signals.

FIG. 2C shows additional examples of differentiating a desired signal from one or more background signals. The graph 250 shows ultrasonic receiver signals corresponding to photoacoustic responses of a target object, with the vertical axis indicating photoacoustic amplitude in arbitrary units (a.u.) and the horizontal axis indicating time units in microseconds. The curves 255, 260, 265 and 270 indicate amplitudes of ultrasonic receiver signals corresponding to photoacoustic responses of a target object to light having peak amplitudes at wavelengths of 875 nm, 800 nm, 725 nm and 650 nm, corresponding to skin absorption of 0.02, 0.04, 0.06 and 0.08 $mm^{-1}$, respectively.

In these examples, the peaks and troughs shown in the graph 250 during the first 1.7 microseconds correspond to EMI and to photoacoustic responses of one or more skin layers. Such reflections may be considered to be examples of background signals. One may observe that the portions of the curves 255-270 corresponding to EMI overlay one another, whereas the portions of the curves 255-270 corresponding to skin vary significantly, primarily due to the skin's differing absorption of light of different wavelengths.

Figure 3:
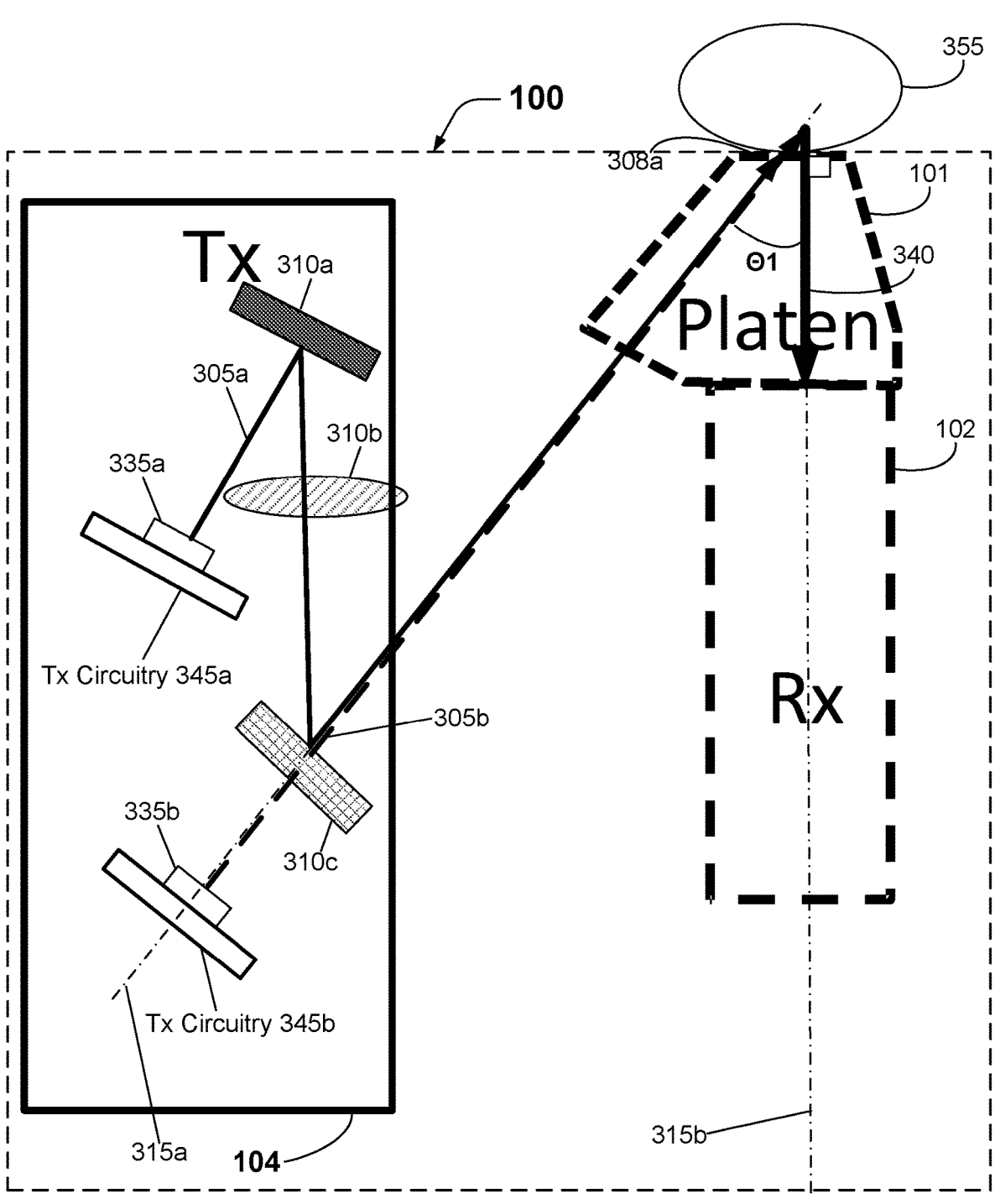
FIG. 3 shows components of an apparatus according to some disclosed implementations.

FIG. 3 shows components of an apparatus according to some disclosed implementations. As with other figures provided herein, the numbers, types and arrangements of elements shown in FIG. 3 are merely presented by way of example. In this example, the apparatus 100 is an instance of the apparatus 100 shown in FIG. 1. According to this example, the apparatus 100 includes a platen 101, a receiver system 102 and a light source system 104. In this example, an outer surface 308a of the platen 101 is configured to receive a target object 355, which is a finger in this example.

According to this example, the light source system 104 includes a light-emitting component 335a and corresponding light source system circuitry 345a, a light-emitting component 335b and corresponding light source system circuitry 345b, and light-directing elements 310a, 310b and 310c. According to this example, the light-directing elements 310a, 310b and 310c are a mirror, a lens and a beam splitter, respectively. The light-emitting components 335a and 335b may, for example, include one or more light-emitting diodes, one or more laser diodes, one or more VCSELs, one or more edge-emitting lasers, one or more neodymium-doped yttrium aluminum garnet (Nd:YAG) lasers, or combinations thereof.

In this example, the light-emitting component 335a is configured to emit the light 305a and the light-emitting component 335b is configured to emit the light 305b (shown as a heavy dashed line in FIG. 3). According to this example, the light 305a and the light 305b have amplitude peaks at different wavelengths. In some implementations, the light source system 104 may include a light guide configured to direct light from the light source system 104 towards the platen 101.

According to this example, the light source system 104 is configured to direct the light 305a and the light 305b towards the target object 355 along the same axis, which is the axis 315a in this instance. In this example, the axis 315a is at an angle $\Theta 1$ relative to the axis 315b, which is normal to the outer surface 308a of the platen 101. In some examples, the angle $\Theta 1$ may be in a range from 10 degrees to 60 degrees. In this example, the light-directing element 310a is configured to reflect light emitted by the light-emitting component 335a towards the light-directing element 310b. According to this example, the light-directing element 310c is configured to direct light emitted by the light-emitting component 335a and the light-emitting component 335b along the axis 315a. In this example, the light-directing element 310b is configured to focus light reflected by the light-directing element 310a. In some instances, the light-directing element 310b may be configured to focus light reflected by the light-directing element 310a on the light-directing element 310c.

In some alternative examples, the light source system 104 may be configured to direct the light 305a and the light 305b towards the target object 355 substantially along the same axis. In this context, "substantially along the same axis" may mean within plus or minus 5 degrees, within plus or minus 10 degrees, within plus or minus 15 degrees, etc.

In this example, the light 305a and the light 305b produce photoacoustic responses in the target object 355, causing acoustic waves 340 be emitted by the target object 355. At least some of the acoustic waves 340 are ultrasonic waves that travel along the axis 315b towards the receiver system 102. Accordingly, the acoustic waves 340 cause ultrasonic receiver signals from the receiver system 102 corresponding to photoacoustic responses of the target object 355 to the light 305a and the light 305b.

Figure 4:
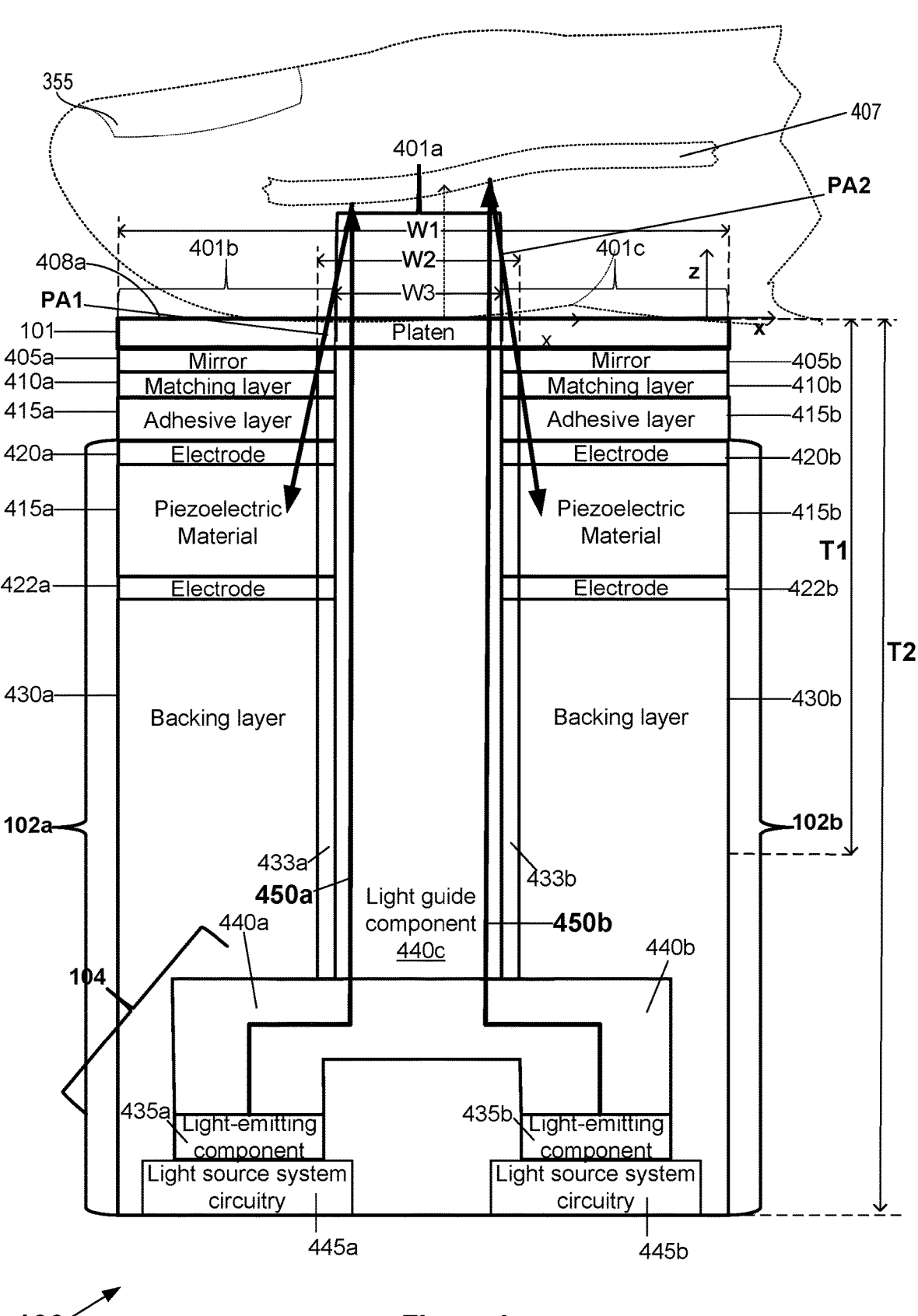
FIG. 4 shows example components of an apparatus according to some alternative implementations.

FIG. 4 shows example components of an apparatus according to some alternative implementations. As with other figures provided herein, the numbers, types and arrangements of elements shown in FIG. 4 are merely presented by way of example. In this example, the apparatus 100 is an instance of the apparatus 100 shown in FIG. 1. According to this example, the apparatus 100 includes a platen 101, a receiver system 102 and a light source system 104. In this example, an outer surface 408a of the platen 101 is configured to receive a target object, which is the finger 355 in this example.

In this example, the light source system 104 includes light-emitting components 435a and 435b, as well as light source system circuitry 445a and 445b. The light-emitting components 435a and 435b may, for example, include one or more light-emitting diodes, one or more laser diodes, one or more VCSELs, one or more edge-emitting lasers, one or more neodymium-doped yttrium aluminum garnet (Nd: YAG) lasers, or combinations thereof. In this example, the light source system 104 includes L instances of light-emitting components, where L is an integer greater than 1. L equals 2 in this example. In other examples, L may be greater than 2. Accordingly, in this example the light source system includes at least a second light-emitting component and at least a second light guide component.

According to this example, the light source system 104 includes the light guide component 440a, which is configured to transmit the light 450a from the light-emitting component 435a to the light guide component 440c. In this example, the light source system also includes the light guide component 440b, which is configured to transmit the light 450b from the light-emitting component 435b to the light guide component 440c. Accordingly, in this example the light source system includes at least a second light-emitting component and at least a second light guide component, the second light guide component being configured to transmit light from the second light-emitting component to at least a portion of the first light guide component.

Although the light guide components 440a and 440b are shown as having 90-degree bends, these are merely examples. According to some other implementations—including but not limited to the examples shown in FIGS. 8A and 8B—the light guide components 440a and 440b may have different shapes. In some implementations, the light guide components 440a and 440b may include flexible material, such as one or more optical fibers, allowing the light guide components 440a and 440b to form arcuate shapes and more gradual bends.

According to this example, the receiver system 102, is, or includes, an ultrasonic receiver system. In this example, the receiver system 102 includes the receiver stack portion 102a and the receiver stack portion 102b. In this example, the receiver stack portion 102a includes piezoelectric material 415a, an electrode layer 420a on a first side of the piezoelectric material 415a and an electrode layer 422a on a second side of the piezoelectric material 415a. According to some examples, a layer of anisotropic conductive film (ACF) may reside between each of the electrode layers 420a and 420b and the piezoelectric material 415a. In this example, the electrode layer 422a resides between piezoelectric material 415a and a backing layer 430a. The electrode layers 420a and 420b include conductive material, which may be, or may include, a conductive metal such as copper in some instances. The electrode layers 420a and 420b may be electrically connected to receiver system circuitry, which is not shown in FIG. 4. The receiver system circuitry may be regarded as a portion of the control system 106 that is described herein with reference to FIG. 1, as a part of the receiver system 102, or both. The piezoelectric material 415a may, for example, include a polyvinylidene difluoride (PVDF) polymer, a polyvinylidene fluoride-trifluoroethylene (PVDF-TrFE) copolymer, aluminum nitride (AlN), lead zirconate titanate (PZT), piezoelectric composite material, such as a 1-3 composite, a 2-2 composite, a 3-3 composite, etc., or combinations thereof.

The backing layers 430a and 430b may be configured to suppress at least some acoustic artifacts and may provide a relatively higher signal-to-noise ratio (SNR) than receiver systems 102 that lack a backing layer. In some examples, the backing layers 430a and 430b may include metal, epoxy, or a combination thereof. According to this example, the backing layers 430a and 430b extend from the electrode layers 422a and 422b to the base of the light source system circuitry 445a and 445b. In some examples, the backing layers 430a and 430b may be portions of a continuous structure, such as a ring structure. In some examples, the backing layers 430a and 430b may surround the light source system circuitry 445a and 445b, the light-emitting components 435a and 435b, and the light guide components 440a and 440b.

In this example, the receiver stack portion 102b includes piezoelectric material 415b, an electrode layer 420b on a first side of the piezoelectric material 415b and an electrode layer 422b on a second side of the piezoelectric material 415b. Here, the electrode layer 422b resides between the piezoelectric material 415b and a backing layer 430b. According to this example, the receiver stack portion 102a resides proximate a first side of the light guide component 440c and the receiver stack portion 102b resides proximate a second side of the light guide component 440c. In this example, the piezoelectric materials 415a and 415b are configured to produce electric signals in response to received acoustic waves, such as the photoacoustic waves PA1 and PA2.

The light guide components 440a, 440b and 440c may include any suitable material, or combination of materials, for causing at least some of the light emitted by the light-emitting components 435a and 435b to propagate within the light guide components 440a, 440b and 440c, for example due to total internal reflection between one or more core materials and one or more cladding materials of the light guide components 440a, 440b and 440c. In such examples, the core material(s) will have a higher index of refraction than the cladding material(s). In one specific and non-limiting example, the core material may have an index of refraction of approximately 1.64 and the cladding material may have an index of refraction of approximately 1.3. In some examples, the core material(s) may include glass, silica, quartz, plastic, zirconium fluoride, chalcogenide, or combinations thereof. According to some examples, the cladding material(s) may include polyvinyl chloride (PVC), acrylic, polytetrafluoroethylene (PTFE), silicone or fluorocarbon rubber. The light guide components 440a, 440b and 440c may, in some examples, include one or more optical fibers. As used herein, the terms "light guide" and "light pipe" may be used synonymously.

In some examples, the width W3 of the light guide component 440c may be in the range of 0.25 mm to 3 mm, for example 0.5 mm, 1.0 mm, 1.5 mm, etc. According to some examples, the width W2 of the space between the receiver stack portion 102a and the receiver stack portion 102b may be in the range of 0.5 mm to 5 mm, for example 1.0 mm, 1.5 mm, 2 mm, 2.5 mm, etc. In some examples, the space 433a between the receiver stack portion 102a and the light guide component 440c and the space 433b between the receiver stack portion 102b and the light guide component 440c, if any—in other words, the space(s) between W2 and W3, if any—may include light-absorbing material. According to some examples, the spaces 433a and 433b, if any, may include air. In some examples, the spaces 433a and 433b, if any, may include sound-absorbing material, preferably sound-absorbing material having a relatively low Grüneisen parameter.

In this example, the light source system 104 is configured to emit light through a first area of the platen towards a target object that is in contact with the first area of the platen 101. According to this example, the light source system 104 is configured to transmit light-represented in FIG. 4 by the light rays 450a and 450b—through the light guide component 440c and the platen area 401a towards the finger 355, which is in contact with the platen area 401a. In this example, an arterial wall of the artery 407 produces the photoacoustic waves PA1 and PA1 responsive to the light rays 450a and 450b, respectively.

The platen 101 may include any suitable material, such as glass, acrylic, polycarbonate, combinations thereof, etc. In some examples, the width W1 of the platen 101 may be in the range of 2 mm to 10 mm, for example 4 mm, 5 mm, 6 mm, etc. According to some examples, the thickness of the platen 101 (in the z direction of the coordinate system shown in FIG. 4) may be in the range of 50 microns to 500 microns, for example 150 microns, 200 microns, 250 microns, 300 microns, etc.

In this example, the platen 101 includes platen areas 401a, 401b and 401c. In this example, the platen area 401a resides adjacent the light guide component 440c. Accordingly, at least the platen area 401a includes transparent material in this example. According to some examples, the platen 101 may include one or more anti-reflective layers. In some examples, one or more anti-reflective layers may reside on the platen 101, or proximate the platen 101, for example on or proximate the outer surface 408a.

According to this example, the platen area 401b resides proximate the receiver stack portion 102a and the platen area 401c resides proximate the receiver stack portion 102c. In this example, a mirror layer 405a, a matching layer 410a and an adhesive layer 415a reside between the platen area 401b and the receiver stack portion 102a. Similarly, in this example a mirror layer 405b, a matching layer 410b and an adhesive layer 415b reside between the platen area 401c and the receiver stack portion 102b. The matching layers 410a and 410b may have an acoustic impedance that is selected to reduce the reflections of acoustic waves caused by the acoustic impedance contrast between one or more layers of the receiver stack portions 102a and 102b that are adjacent to, or proximate, the matching layers 410a and 410b. According to some examples, the matching layers 410a and 410b may include polyethylene terephthalate (PET). In some examples, the adhesive layers 415a and 415b may include pressure-sensitive adhesive (PSA) material.

In the example shown in FIG. 4, the apparatus has a thickness (along the z axis) of T1 from the top of the platen to the base of the backing layers 430a and 430b, and has a thickness of T2 from the top of the platen to the base of the light source system circuitry. In some examples, T2 may be in the range of 2 mm to 10 mm. According to some examples, T1 may be in the range of 1 mm to 8 mm. The backing layers 430a and 430b may be in the range of 3 mm to 7 mm in thickness, such as 4.5 mm, 5.0 mm, 5.5, mm, etc. Accordingly, implementations that lack a backing layer, or backing layers, may be substantially thinner than implementations that include a backing layer, or backing layers.

Figure 5A:
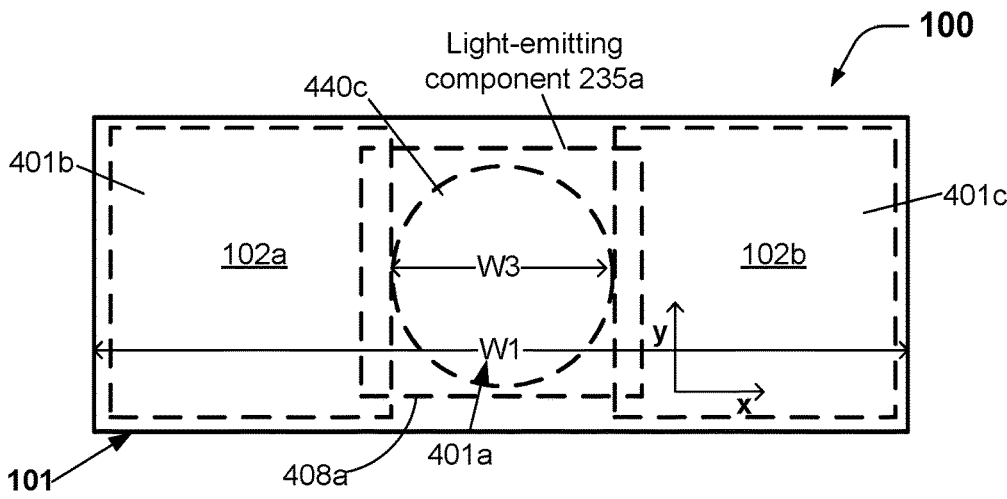
FIGS. 5A, 5B and 5C show different examples of how some components of the apparatus shown in FIG. 4 may be arranged.
Figure 5B:
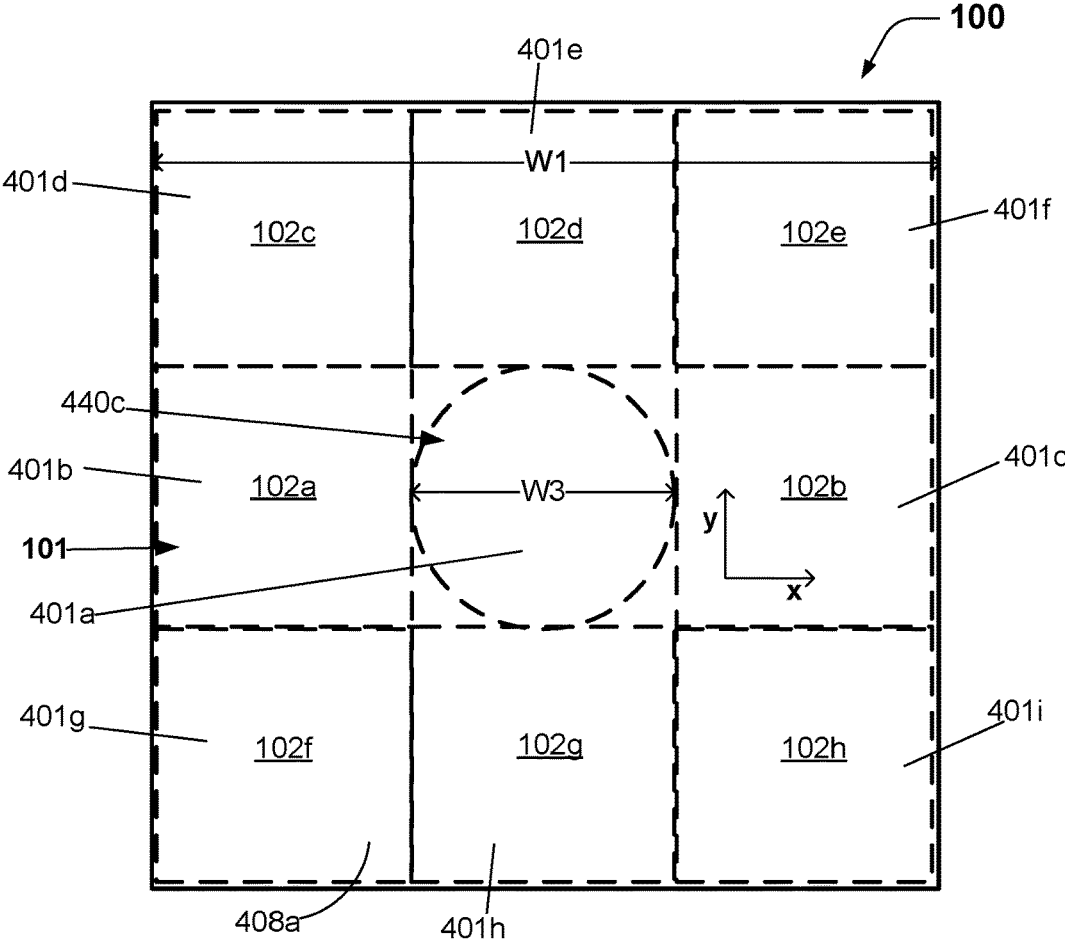
Figures 5C, 5D:
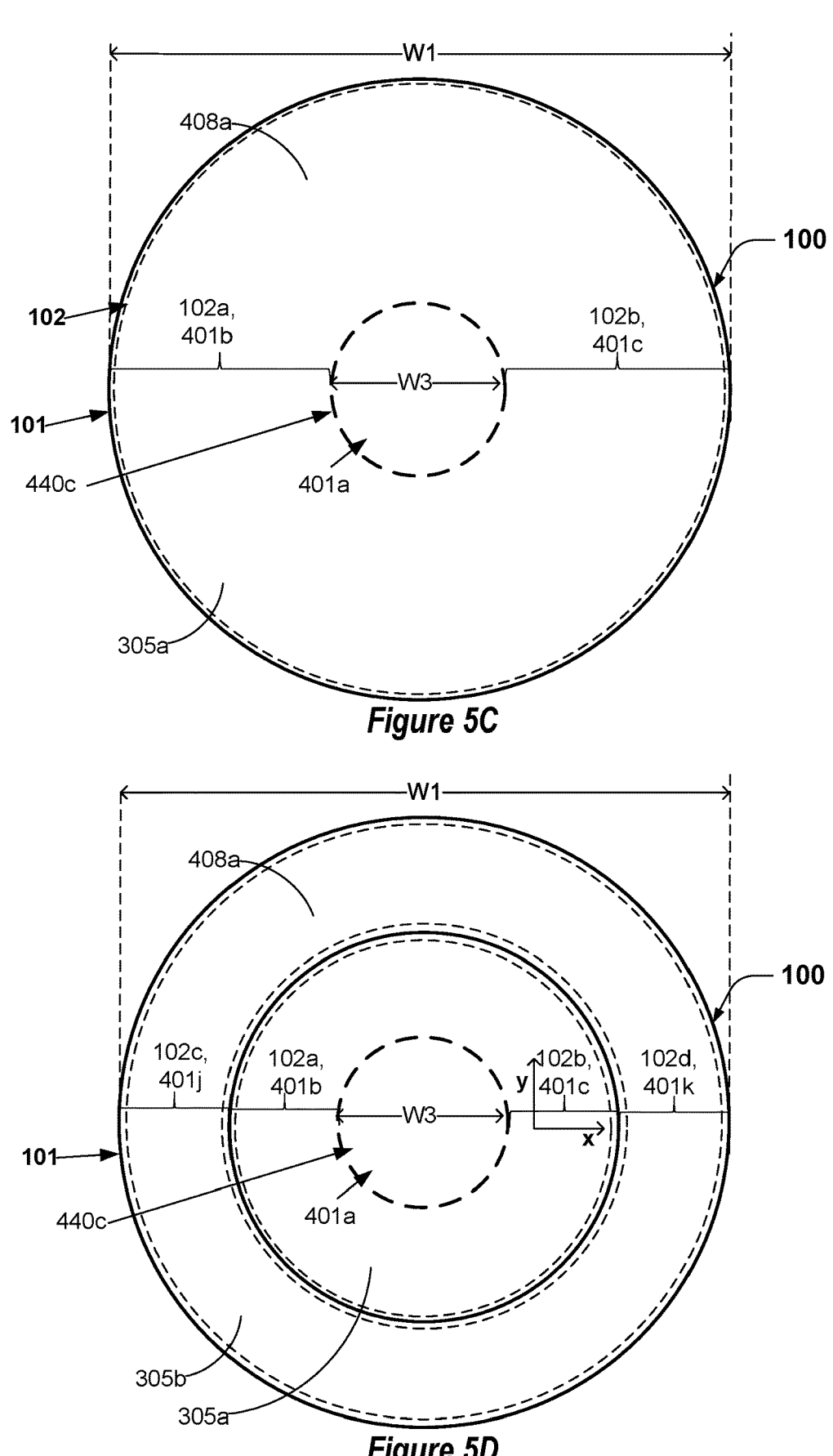
FIG. 5D shows examples of the components of the apparatus shown in FIG. 4 arranged with additional components.

FIGS. 5A, 5B and 5C show different examples of how some components of the apparatus shown in FIG. 4 may be arranged. As with other figures provided herein, the numbers, types and arrangements of elements shown in FIGS. 5A-5C are merely presented by way of example. In these examples, the apparatus 100 is an instance of the apparatus 100 shown in FIGS. 1 and 4. In each of these examples, a top view of the apparatus 100 is shown, with the view being along the z axis of the coordinate system shown in FIG. 4. In these examples, the light guide component 440c is shown to have a circular cross-section. However, in alternative examples the light guide component 440c may have a different cross-sectional shape, such as a square cross-sectional shape, a rectangular cross-sectional shape, a hexagonal cross-sectional shape, etc.

In these examples, the outlines of the receiver stack portion 102a and the receiver stack portion 102b (and, in FIG. 5B, the outlines of the receiver stack portions 102c-102h) are shown in dashes, indicating that these elements are below the outer surface 408a of the platen 101. According to these examples, the receiver stack portion 102a resides proximate a first side of the light guide component 440c and the receiver stack portion 102b resides proximate a second side of the light guide component 440c. In these examples, the receiver stack portion 102a resides proximate (in this example, below, further away from the viewer along the z axis) platen area 102b on a first side of the platen area 102a and the receiver stack portion 102b resides proximate platen area 102c, which is on a second and opposite side of the platen area 102a.

According to the example shown in FIG. 5A, the receiver stack portion 102a and the receiver stack portion 102b are discrete elements of a linear array of receiver stack portions having N receiver elements, with N being 2 in this instance. In alternative examples, N may be greater than 2.

In the example shown in FIG. 5B, the receiver stack portion 102a and the receiver stack portion 102b are discrete elements of a two-dimensional receiver array of receiver stack portions having M receiver elements, with M being 9 in this instance. In alternative examples, M may be greater than or less than 9.

According to the example shown in FIG. 5C, the receiver stack portion 102a and the receiver stack portion 102b are portions of a receiver stack ring 305a. In this example, the receiver stack ring 305a is configured to surround the light guide component 440c. According to this example, an annular area of the platen 301 proximate (in this example, above, closer to the viewer along the z axis) the receiver stack ring 305a, which includes the platen areas 401b and 401c, is configured to surround the platen area 401a.

FIG. 5D shows examples of the components of the apparatus shown in FIG. 4 arranged with additional components. As with other figures provided herein, the numbers, types and arrangements of elements shown in FIG. 5D are merely presented by way of example. In these examples, the apparatus 100 is an instance of the apparatus 100 shown in FIG. 1. In this example, a top view of the apparatus 100 is shown, with the view being along the z axis of the coordinate system shown in FIG. 4. In this example, the light guide component 440c is shown to have a circular cross-section. However, in alternative examples the light guide component 440c may have a different cross-sectional shape.

In this example, the receiver stack portion 102a and the receiver stack portion 102b are portions of a receiver stack ring 305a. According to this example, the receiver stack ring

305a is configured to surround the light guide component 440c. In this example, the receiver stack ring 305a includes the receiver stack portions 102a and 102b, as well as the platen areas 401b and 401c. According to this example, the receiver stack ring 305b is configured to surround the receiver stack ring 305a. In this example, the receiver stack ring 305b includes the receiver stack portions 102c and 102d, as well as the platen areas 401j and 401k.

Figure 6:
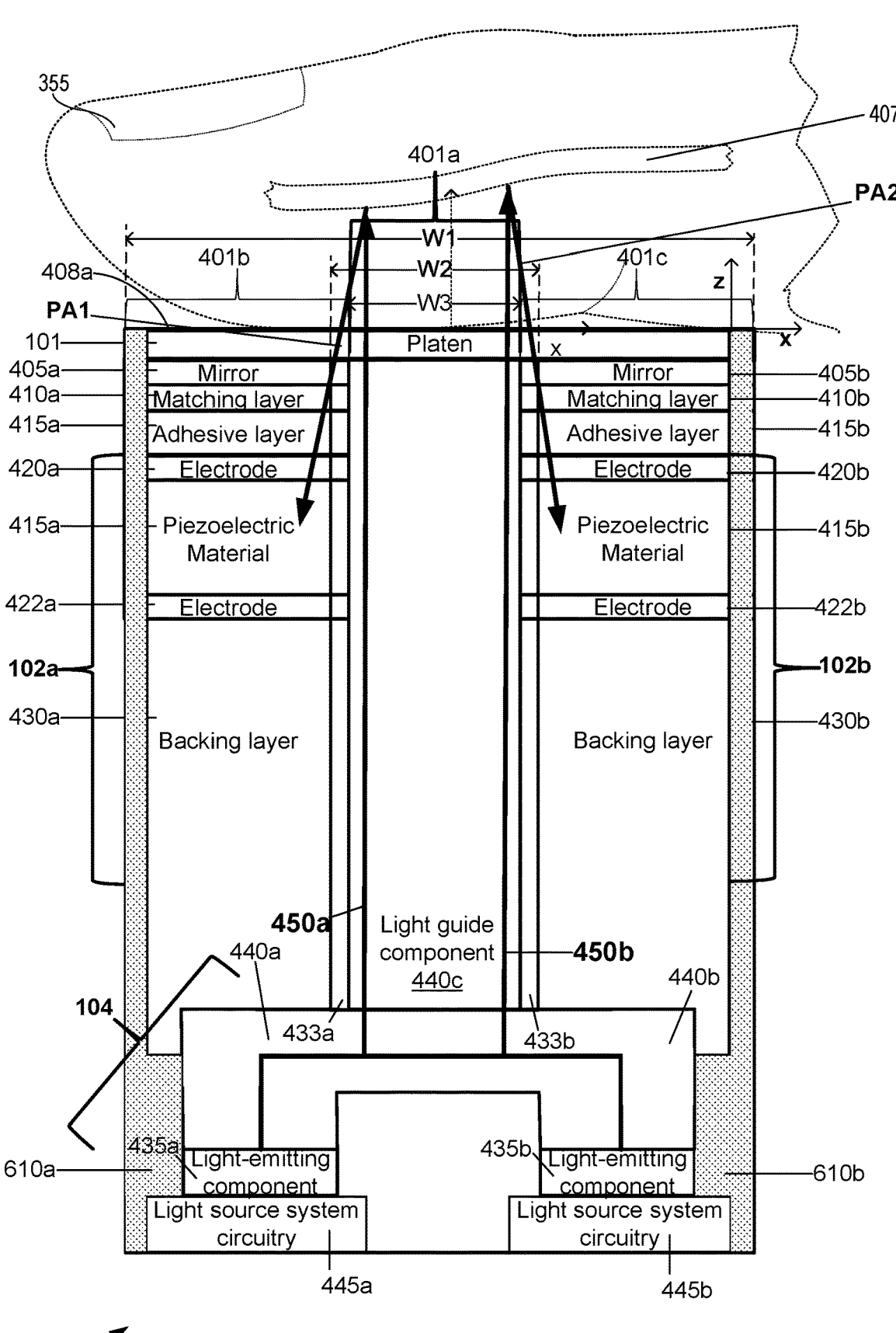
FIG. 6 shows example components of an apparatus according to some alternative implementations.

FIG. 6 shows example components of an apparatus according to some alternative implementations. As with other figures provided herein, the numbers, types and arrangements of elements shown in FIG. 6 are merely presented by way of example. In this example, the apparatus 100 is an instance of the apparatus 100 shown in FIG. 1. According to this example, the apparatus 100 includes a platen 101, a receiver system 102 and a light source system 104. In this example, an outer surface 408a of the platen 101 is configured to receive a target object, which is the finger 355 in this example.

The apparatus 100 shown in FIG. 6 is substantially similar to the apparatus 100 shown in FIG. 4 and described above. Therefore, the detailed description of components in FIG. 6 that are the same as their counterparts in FIG. 4 will not be repeated here. Instead, this discussion will focus on the differences between the apparatus 100 of FIG. 4 and the apparatus 100 of FIG. 6.

According to this example, the backing layers 430a and 430b do not extend from the electrode layers 422a and 422b to the base of the light source system circuitry 445a and 445b, as shown in FIG. 4. Instead, the backing layers 430a and 430b are adjacent only to portions of the light guide components 440a and 440b, and do not extend to the light-emitting components 435a and 435b or the light source system circuitry 445a and 445b. In some examples, the backing layers 430a and 430b may be portions of a continuous structure, such as a ring structure, that surrounds portions of the light guide components 440a and 440b.

Moreover, in this example, the apparatus 100 includes noise-reducing elements 610a and 610b. The noise-reducing elements 610a and 610b are instances of the noise reduction system 110 that is described with reference to FIG. 1. One type of noise that may be present in the apparatus 100 is electromagnetic interference (EMI) from the light source system circuitry 445a and 445b that may be received by the receiver system 102. In some implementations, at least portions of the noise-reducing element 610a and the noise-reducing element 610b may include EMI-suppressing material.

In this example, the noise-reducing elements 610a and 610b extend from the outer surface 408a to the base of the light source system circuitry 445a and 445b. According to some alternative examples, the noise-reducing elements 610a and 610b extend from the base of the platen 101 to the base of the light source system circuitry 445a and 445b. In some examples, the noise-reducing elements 610a and 610b may be portions of a continuous structure, such as a ring structure. In some such examples, the noise-reducing elements 610a and 610b may be portions of a continuous structure that surrounds all of the layers from the platen 101 to the light source system circuitry 445a and 445b, or all of the layers from the mirrors 405a and 405b to the light source system circuitry 445a and 445b.

Figure 7:
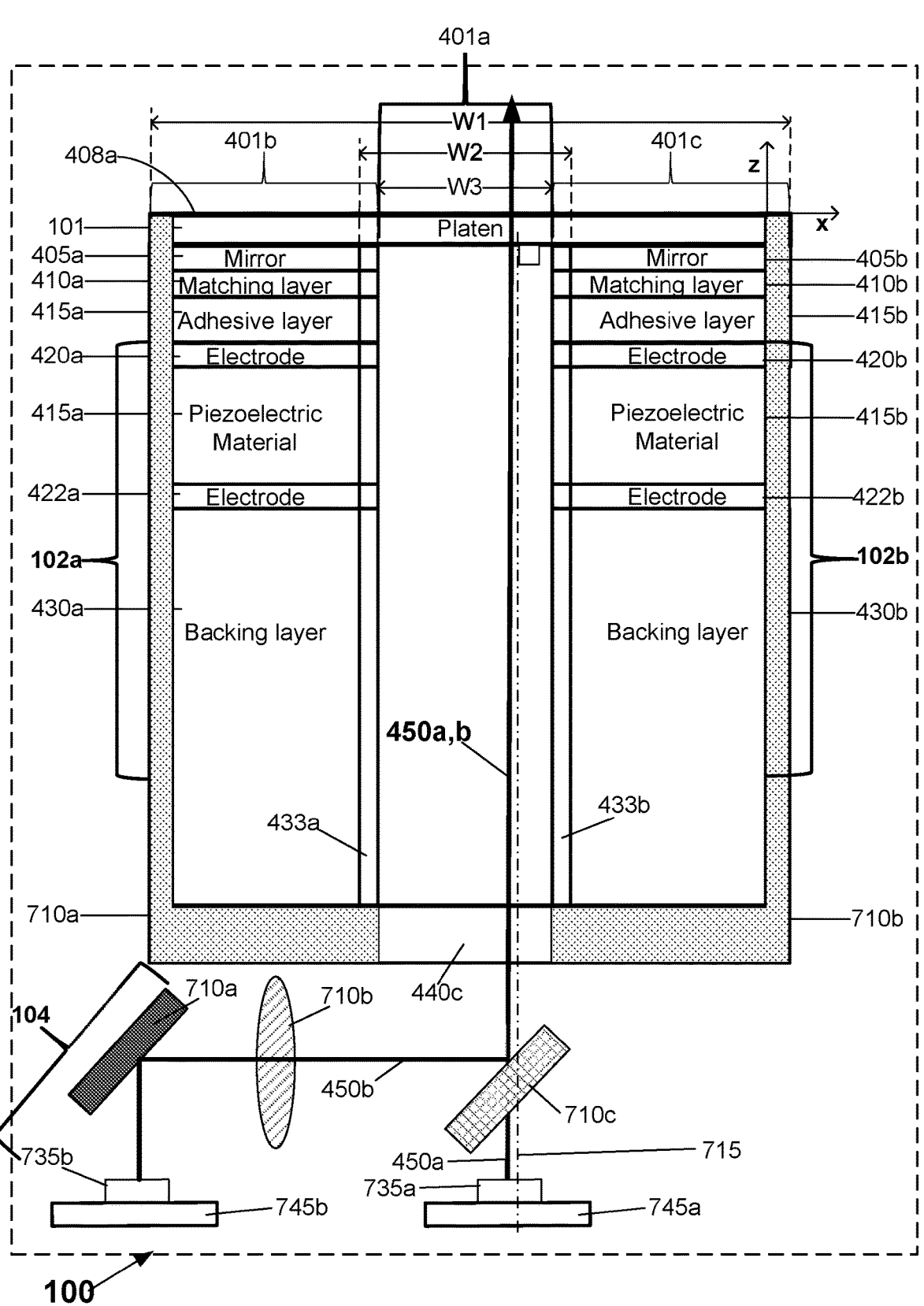
FIG. 7 shows example components of an apparatus according to some alternative implementations.

FIG. 7 shows example components of an apparatus according to some alternative implementations. As with other figures provided herein, the numbers, types and arrangements of elements shown in FIG. 7 are merely presented by way of example. In this example, the apparatus 100 is an instance of the apparatus 100 shown in FIG. 1. According to this example, the apparatus 100 includes a platen 101, a receiver system 102 and a light source system 104. In this example, an outer surface 408a of the platen 101 is configured to receive a target object, which is the finger 355 in this example.

The apparatus 100 shown in FIG. 7 is substantially similar to the apparatus 100 shown in FIG. 6 and described above. The apparatus 100 shown in FIG. 7 also includes light-directing elements similar to the light-directing elements 310a, 310b and 310c of FIG. 3. Therefore, the detailed description of components in FIG. 7 that are the same as their counterparts in FIGS. 3 and 6 will not be repeated here. Instead, this discussion will focus on the differences between the apparatus 100 of FIGS. 3 and 6, and the apparatus 100 of FIG. 7.

According to this example, the light source system 104 includes the light guide component 440c of FIG. 6, but does not include the light guide components 440a and 440b. In this example, light 450a and 450b from the light-emitting elements 735a and 735b, respectively, is directed towards the platen 101 by the light-directing elements 710a, 710b and 710c. According to this example, the light-directing elements 710a, 710b and 710c are a mirror, a lens and a beam splitter, respectively. In this example, the light source system 104 is configured to direct light 450a and 450b towards the platen 101 along an axis 715 that is perpendicular to the platen 101 and is parallel to the long axis of the light guide component 440c, which corresponds to the z axis in this instance.

Also, unlike the example shown in FIG. 3, the receiver system 102 receives at least some acoustic waves produced by the light 450a and 450b along axes parallel to, or substantially parallel to, the axis along which the light 450a and 450b is transmitted, which is the axis 715 of FIG. 7 in this example. In this context, "substantially parallel to" the axis 715 may mean plus or minus 5 degrees, plus or minus 10 degrees, plus or minus 15 degrees, plus or minus 20 degrees, etc.

Like the noise-reducing elements 610a and 610b of FIG. 6, the noise-reducing elements 710a and 710b are instances of the noise reduction system 110 that is described with reference to FIG. 1. However, according to this example, the noise-reducing elements 710a and 710b are configured differently than the noise-reducing elements 610a and 610b of FIG. 6. In the example shown in FIG. 7, the noise-reducing elements 710a and 710b do not extend to the base of the light source system circuitry 445a and 445b and do not surround the light source system circuitry 445a and 445b or the light-emitting elements 735a and 735b. Moreover, in the example shown in FIG. 7, portions of the noise-reducing elements 710a and 710b extend between the backing layers 430a and 430b and at least some portions of the light source system 104. As noted elsewhere herein, in some instances the backing layers 430a and 430b may be portions of a continuous structure, such as a ring structure, that surrounds the light guide component 440c. In some such examples, portions of the noise-reducing elements 710a and 710b may extend in a continuous structure, such as a ring structure, between the backing layers 430a and 430b and at least some portions of the light source system 104.

Figure 8A:
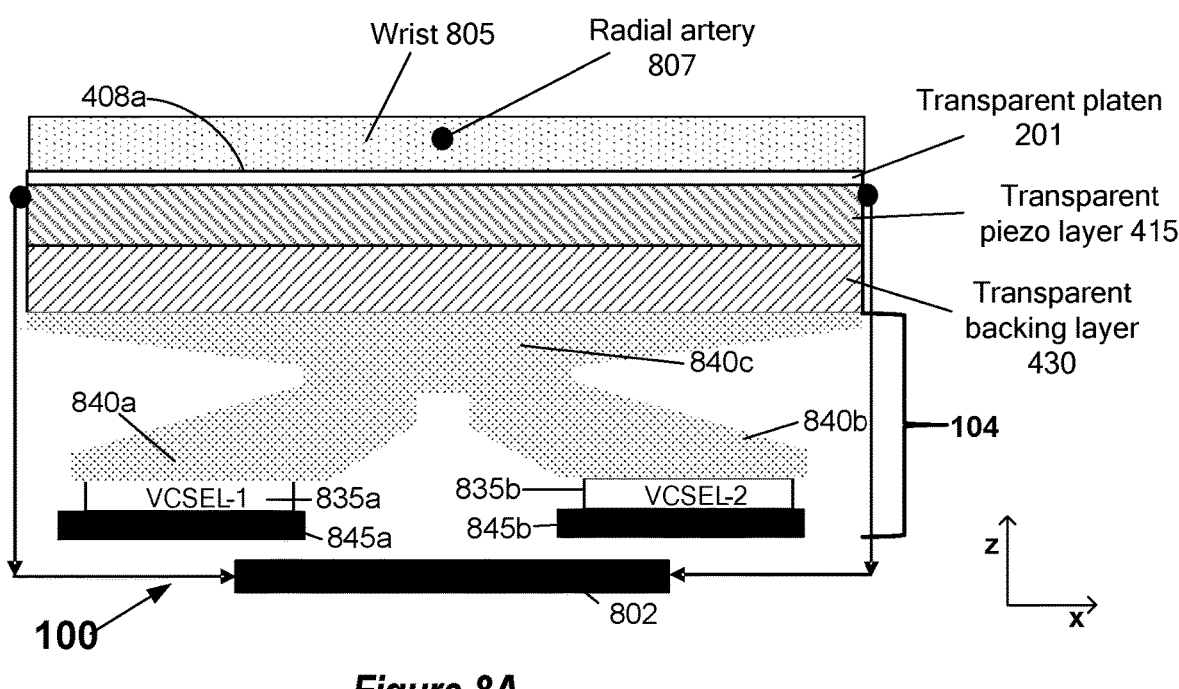
FIGS. 8A and 8B shows example components of an apparatus according to some alternative implementations.
Figure 8B:
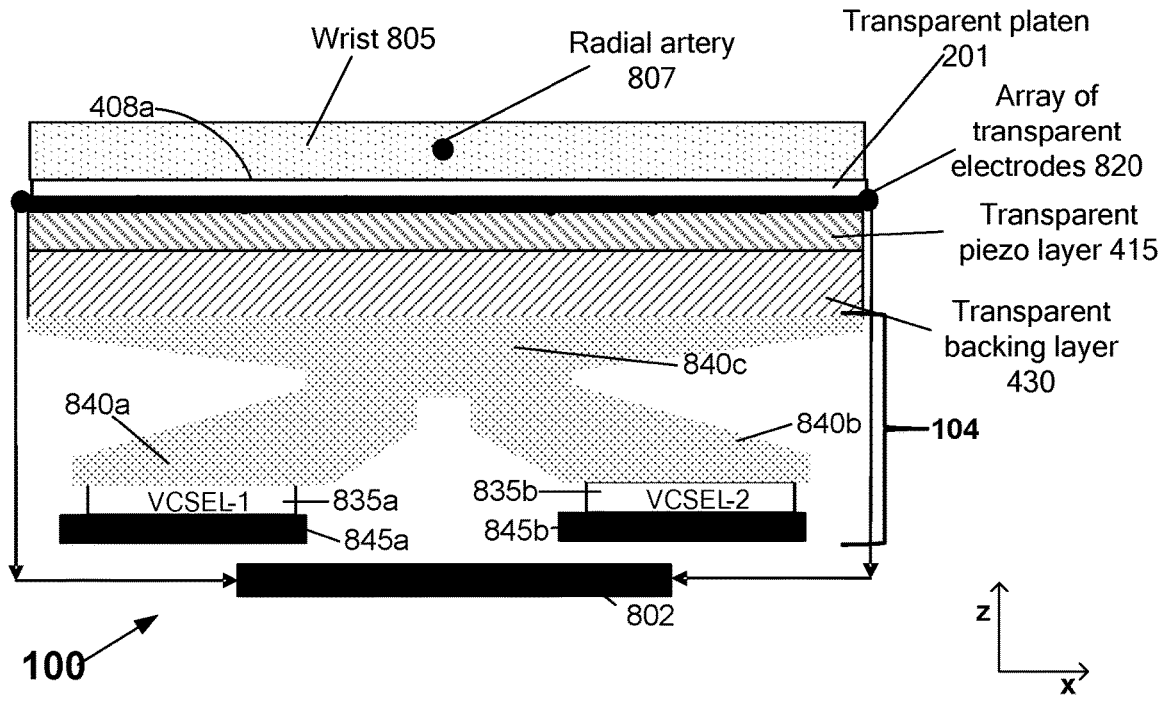

FIGS. 8A and 8B shows example components of an apparatus according to some alternative implementations. As with other figures provided herein, the numbers, types and arrangements of elements shown in FIGS. 8A and 8B are merely presented by way of example. In these examples, the apparatus 100 is an instance of the apparatus 100 shown in FIG. 1. According to these examples, the apparatus 100 includes a platen 101, a receiver system 102 and a light source system 104. In these examples, an outer surface of the platen 101 is configured to receive a target object, which is a wrist 805 that includes a radial artery 807 in these examples.

The examples shown in FIGS. 8A and 8B have some similarities to the apparatus 100 shown in FIG. 4 and described above. For example, the examples shown in FIGS. 8A and 8B include light guide components 840a, 840b and 840c, which have similar functions to those of the light guide components 440a, 440b and 440c of FIG. 4: like the light guide components 440a, 440b and 440c, the light guide components 840a, 840b and 840c are configured to direct light from the light-emitting elements 835a and 835b—which are VCSELs in this example—towards at least a portion of the outer surface 408a of the platen 101. However, in the examples shown in FIGS. 8A and 8B, the shapes and proportions of the light guide components 840a, 840b and 840c are somewhat different from the light guide components 440a, 440b and 440c of FIG. 4. For example, the light guide component 440c of FIG. 4 has a uniform, or substantially uniform (such as plus or minus 1%, plus or minus 3%, plus or minus 5%, etc.) width as measured in the x direction, whereas the width of the light guide component 840c of FIGS. 8A and 8B increases from a first side proximate the light guide components 840a and 840b to a second side proximate the backing layer 430. In these examples, the width (at least along the x axis) of the light guide component 840c on the second side proximate the backing layer 430 is equal to the width of the backing layer 430.

According to these examples, both the backing layer 430 and the piezoelectric material 415 are transparent. In some such examples, the transparent backing layer 430 may include transparent particles such as glass beads, e.g., spherical beads, other transparent particle shapes, or combinations thereof, in a transparent epoxy. According to some examples, the transparent piezoelectric material 415 may include PVDF. In some examples, the light source system 104 may be configured to provide light through the transparent backing layer 430 and the transparent piezoelectric material 415 to all, or substantially all (such as at least 75%, at least 80%, at least 85%, at least 90%, etc.) of the outer surface 408a of the platen 101.

In the examples shown in FIGS. 8A and 8B, the receiver system circuitry 802 resides below—in other words, farther along the −z direction—the light source system 104. This physical separation between the receiver system circuitry 802 and the piezoelectric material 415 is potentially advantageous, because it can result in relatively less EMI reaching the piezoelectric material 415, as compared to implementations in which the receiver system circuitry 802 resides closer to the piezoelectric material 415.

In the example shown in FIG. 8B, the apparatus includes an array of transparent electrodes 820 residing between the transparent piezoelectric material 415 and the platen 101. In some examples, the array of transparent electrodes 820 may include indium tin oxide (ITO), wider-spectrum transparent conductive oxides (TCOs), conductive polymers, or combinations thereof. According to some examples, the array of transparent electrodes 820 may include a linear array. Alternatively, or additionally, in some examples the array of transparent electrodes 820 may include a two-dimensional array.

Figure 9A:
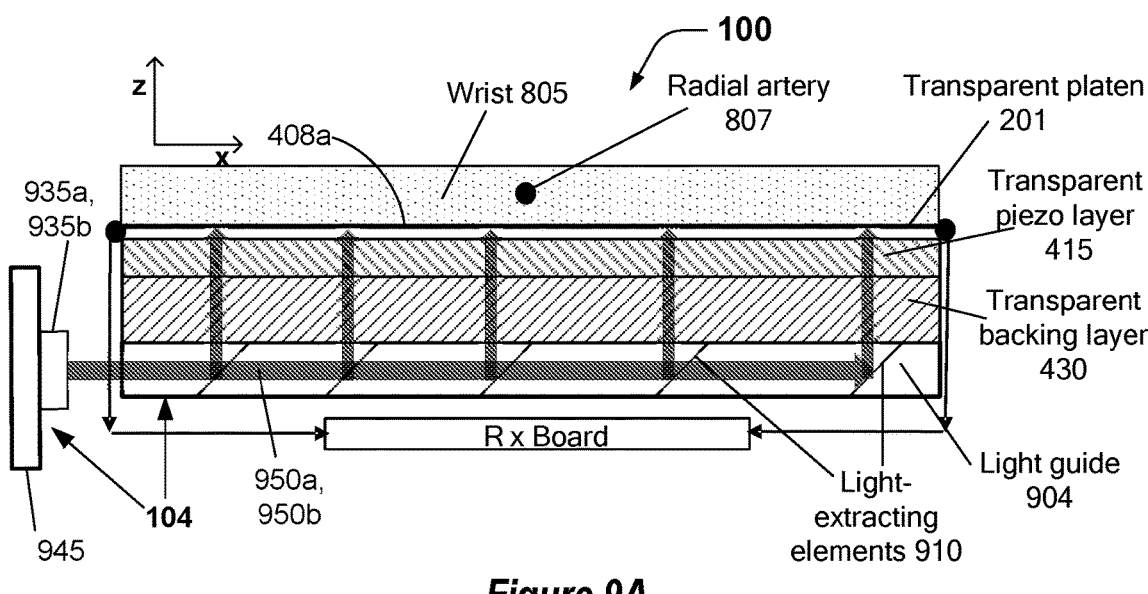
FIGS. 9A, 9B and 9C shows example components of an apparatus according to some alternative implementations.
Figure 9B:
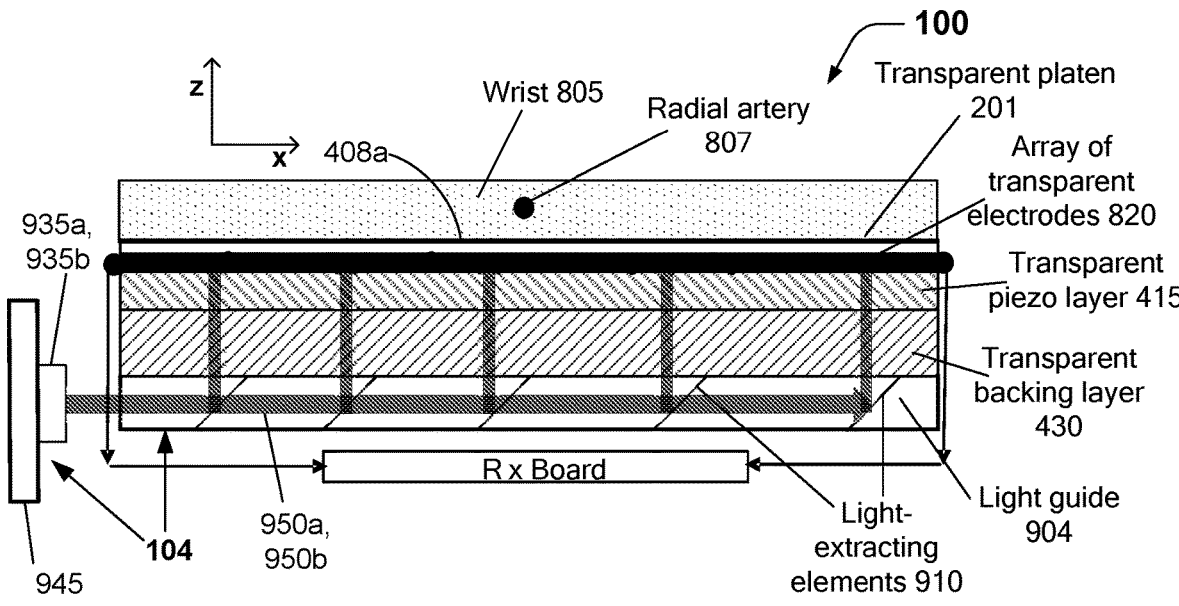
Figure 9C:
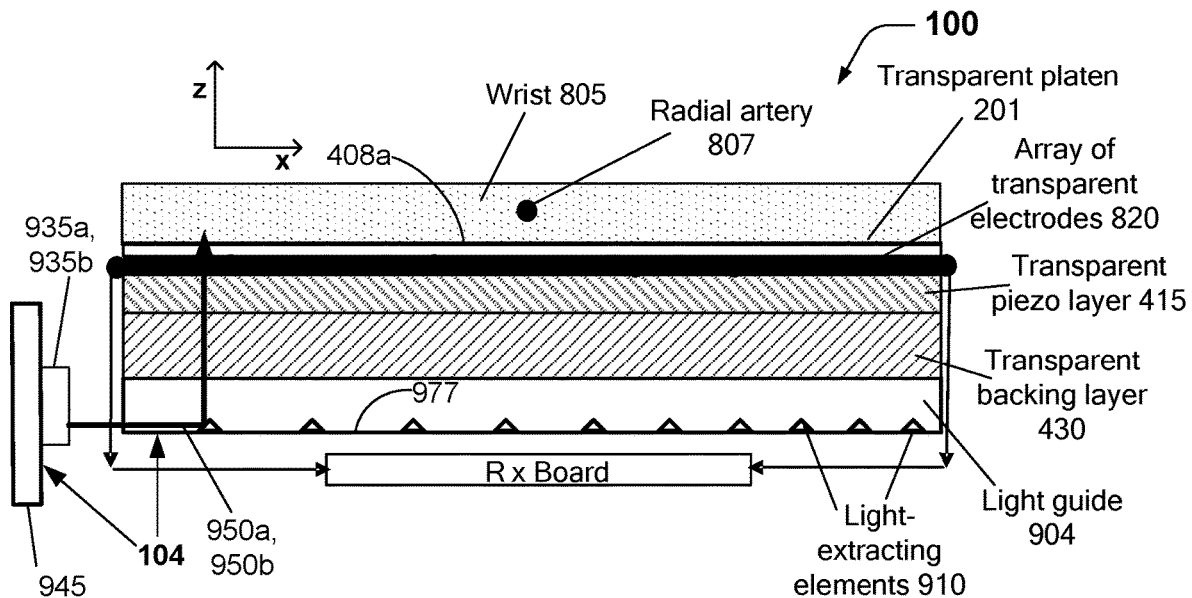

FIGS. 9A, 9B and 9C show example components of devices according to some alternative implementations. As with other figures provided herein, the numbers, types and arrangements of elements shown in FIGS. 9A-9C are merely presented by way of example. In these examples, the apparatus 100 is an instance of the apparatus 100 shown in FIG. 1. According to these examples, the apparatus 100 includes a platen 101, a receiver system 102 and a light source system 104. In these examples, an outer surface of the platen 101 is configured to receive a target object, which is a wrist 805 that includes a radial artery 807 in these examples.

In the examples shown in FIG. 9A-9C, the light guide system 104 includes a light guide 904 that is configured to direct light 950a and 950b from the light-emitting elements 935a and 935b, respectively, in a direction that is parallel to, or substantially parallel to, the platen 101. According to these examples, the light-emitting element 935a is configured to emit light having a peak amplitude at a first wavelength and the light-emitting element 935b is configured to emit light having a peak amplitude at a second wavelength. In these examples, the light guide system 104 is configured to direct light 950a and 950b substantially along the x axis, which in these examples is oriented parallel to the outer surface 408a of the platen 101. In this context, "substantially parallel to" may mean within 5 degrees of being parallel, within 10 degrees of being parallel, within 15 degrees of being parallel, within 20 degrees of being parallel, etc.

According to some examples, the light-emitting element 935a, the light-emitting element 935b, or both, may be positioned on different sides of the apparatus 100, such as opposing sides or adjacent sides. In some examples, the light-emitting element 935a may reside on one side of the apparatus 100 and the light-emitting element 935b may reside on another side of the apparatus 100. In some examples, the light-emitting element 935a and the light-emitting element 935b may both reside on 2 or more sides of the apparatus 100. According to some examples, the light-emitting elements 935a and 935b may be arranged as shown in FIG. 10B.

According to these examples, the light guide system 104 includes a plurality of light-extracting elements 910 residing within the light guide 904. In these examples, the light-extracting elements 910 are configured to direct light out of the light guide 904 towards the platen 101. In some implementations, the light-extracting elements 910 may be, or may include, beam splitters, mirrors or other reflective structures, etc. In the examples shown in FIGS. 9A and 9B, the light-extracting elements 910 include beam splitters. Alternatively, or additionally, in some implementations the light-extracting elements 910 may be, or may include, one or more indentations in, protuberances of, or structures formed on, a light guide surface. In some such examples, the light-extracting elements 910 may be, or may include, one or more three-dimensional shapes formed from indentations in, protuberances of, or structures formed on, a light guide surface.

In the example shown in FIG. 9C, the light-extracting elements 910 include reflective structures formed on a light guide surface 977. According to this example, the reflective structures are triangular when viewed in a cross-section in the x-z plane, as shown in FIG. 9C. However, in alternative implementations the reflective structures may have other shapes.

According to the example shown in FIG. 9C, the light-extracting elements 910 are arranged with unequal spacing within the light guide 904. In this example, light-extracting elements 910 located farther from the light-emitting devices 935a and 935b are spaced closer together than light-extracting elements 910 located closer to the light-emitting devices 935a and 935b. Having light-extracting elements 910 that are farther from a light source spaced farther apart than light-extracting elements 910 located closer to the light source can provide a relatively more uniform illumination of the outer surface of the platen 101 and of a target object in contact with this surface, as compared to implementations in which identical light-extracting elements 910 are equally spaced. In some other implementations, a relatively more uniform illumination of the outer surface of the platen 101 may be achieved by including light-extracting elements 910 that are farther from a light source that are configured to extract relatively more light than light-extracting elements 910 that are closer to the light source, for example, by providing relatively larger reflective structures relatively farther from the light source.

According to some examples, a two-dimensional array of the light-extracting elements 910 may provide light to all, or substantially all (such as at least 75%, at least 80%, at least 95%, at least 90%, etc.) of the outer surface 408a of the platen 101. In some such examples, the two-dimensional array of light-extracting elements 910 may provide substantially uniform light to an illuminated area of the outer surface 408a of the platen 101. In this context, "substantially uniform" may mean plus or minus 5% of a peak amplitude, plus or minus 10% of a peak amplitude, plus or minus 15% of a peak amplitude, plus or minus 20% of a peak amplitude, etc. In some examples, the light-extracting elements 910 may be arranged as shown in FIGS. 1-6A and as described with reference to FIGS. 1-6A of U.S. Pat. No. 8,545,084, which is hereby incorporated by reference and for all purposes.

According to the examples shown in FIGS. 9A-9C, both the backing layer 430 and the piezoelectric material 415 are transparent. In some examples, the backing layer 430 and the piezoelectric material 415 may be as described above with reference to FIGS. 8A and 8B.

In the examples shown in FIGS. 9A-9C, the receiver system circuitry 802 resides below—in other words, is farther along the −z direction than—the light source system 104. This physical separation between the receiver system circuitry 802 and the piezoelectric material 415 is potentially advantageous, because it can result in relatively less EMI reaching the piezoelectric material 415, as compared to implementations in which the receiver system circuitry 802 resides closer to the piezoelectric material 415.

In the examples shown in FIGS. 9B and 9C, the apparatus 100 includes an array of transparent electrodes 820 residing between the transparent piezoelectric material 415 and the platen 101. In some examples, the array of transparent electrodes 820 may include indium tin oxide (ITO), wider-spectrum transparent conductive oxides (TCOs), conductive polymers, or combinations thereof. According to some examples, the array of transparent electrodes 820 may include a linear array. Alternatively, or additionally, in some examples the array of transparent electrodes 820 may include a two-dimensional array.

Figure 10A:
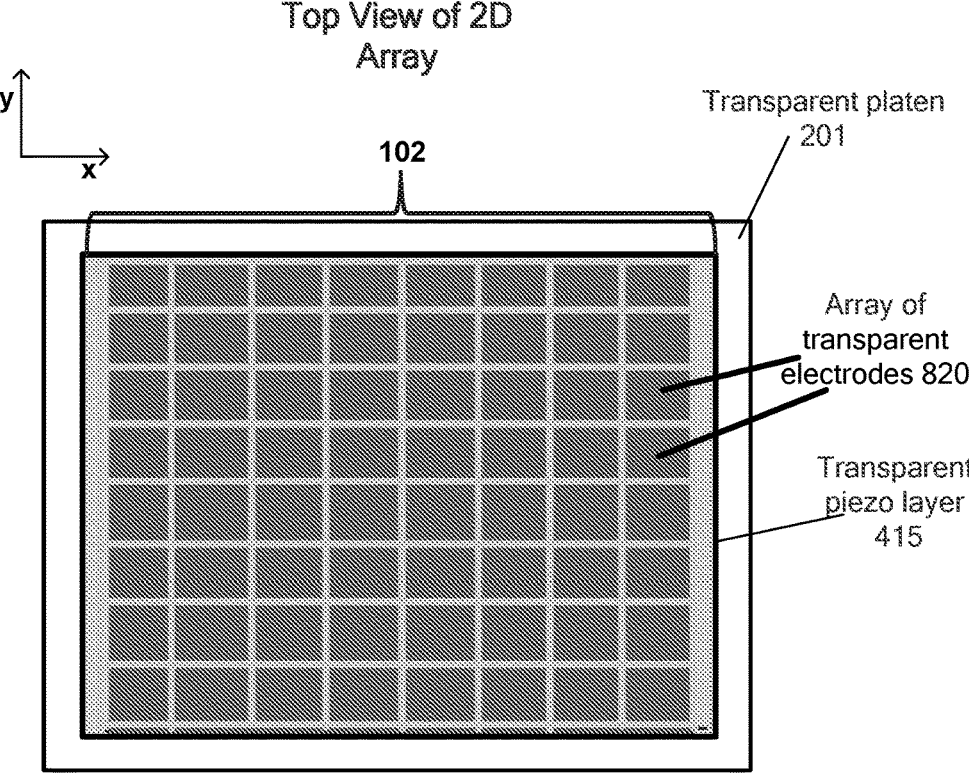
FIGS. 10A and 10B shows example components of an apparatus according to some alternative implementations.
Figure 10B:
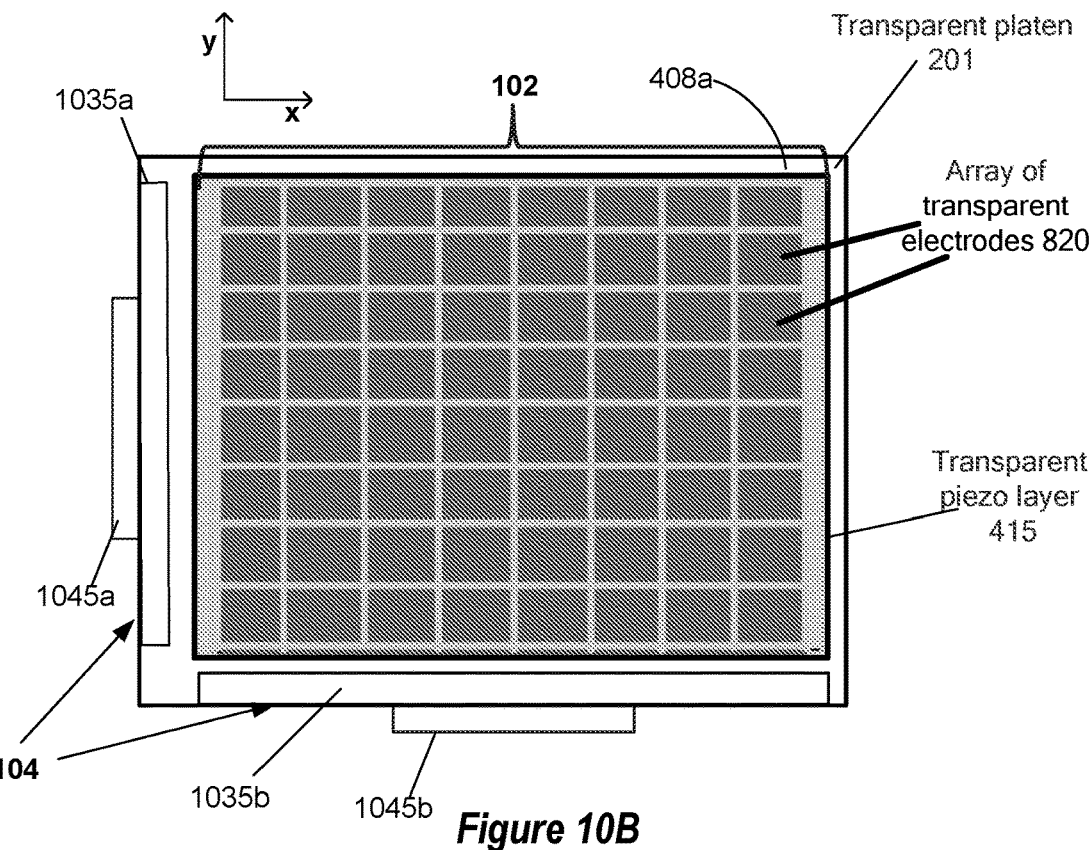

FIGS. 10A and 10B shows example components of an apparatus according to some alternative implementations. As with other figures provided herein, the numbers, types and arrangements of elements shown in FIGS. 10A and 10B are merely presented by way of example. In these examples, the apparatus 100 is an instance of the apparatus 100 shown in FIG. 1. According to these examples, the apparatus 100 includes a transparent platen 101, a receiver system 102 and a light source system 104, though elements of the light source system 104 are not visible in FIG. 10A.

According to the examples shown in FIGS. 10A and 10B, the backing layer 430 if present is transparent. In the examples shown in FIGS. 10A and 10B, the receiver system 102 includes a transparent piezoelectric layer 415 and a two-dimensional array of transparent electrodes 820, which form a two-dimensional array of receiver elements.

Implementations that include an array of receiver elements, including but not limited to implementations that include a two-dimensional array of receiver elements, have various potential advantages. One advantage is that prior knowledge of the precise location of a target of interest, such as a blood vessel, may not be required prior to obtaining ultrasonic or photoacoustic data from a target object. Some receiver elements in the array may be positioned near the target of interest and others may be positioned farther from the target of interest. Some receiver elements may receive relatively stronger signals from the target of interest, some receiver elements may receive relatively weaker signals from the target of interest and other receiver elements may receive such weak signals from the target of interest that the signals are not above a background noise level. Nonetheless, at least some receiver elements may receive sufficiently strong signals from the target of interest that by summing signals received from multiple receiver elements, a clear image of the target of interest may be provided by the apparatus 100.

According to the example shown in FIG. 10B, the light-emitting element 1035a resides on a first side of the apparatus 100 and the light-emitting element 1035b resides on a second side of the apparatus 100, which is an adjacent side in this instance. In some alternative examples, the second side may be an s opposing side. In some examples, the light-emitting element 935a and the light-emitting element 935b may both reside on 2 or more sides of the apparatus 100.

In the example shown in FIG. 10B, the light guide system 104 includes light guides (not shown) that are configured to direct light from the light-emitting elements 1035a and 1035b, respectively, in a direction that is parallel to, or substantially parallel to, the platen 101. In some such examples, the light guides may reside below the transparent piezoelectric layer 415, for example as shown in FIGS. 9A-9C.

According to the example shown in FIG. 10B, the light guide system 104 includes a plurality of light-extracting elements (not shown) residing within the light guide. In these examples, the light-extracting elements are configured to direct light out of the light guide towards the platen 101. In some implementations, the light-extracting elements may be, or may include, beam splitters, mirrors or other reflective structures, etc.

According to some examples, a two-dimensional array of light-extracting elements may provide light to all, or substantially all, of the outer surface 408a of the platen 101. In some such examples, the two-dimensional array of light-extracting elements 910 may provide substantially uniform light to an illuminated area of the outer surface 408a of the platen 101.

FIG. 11 is a flow diagram that shows examples of some disclosed operations. The blocks of FIG. 11 (and those of other flow diagrams provided herein) may, for example, be performed by the apparatus 100 of FIG. 1 or by a similar apparatus. As with other methods disclosed herein, the method outlined in FIG. 11 may include more or fewer blocks than indicated. Moreover, the blocks of methods disclosed herein are not necessarily performed in the order indicated. In some instances, one or more of the blocks shown in FIG. 11 may be performed concurrently.

In this example, block 1105 involves causing a light source system to provide first light of a first wavelength to a target object at a first time. In some examples, block 1105 may involve controlling, by a control system, a light source system—which may be instances of the light source system 104 and the control system 106 of FIG. 1—to emit first light of a first wavelength to a target object on an outer surface of a platen at a first time. The target object may be a finger, a wrist, etc., depending on the particular example. The first light may, for example, be emitted by at least a first light-emitting element of the light source system that is configured to emit light having a peak amplitude at the first wavelength.

According to this example, block 1110 involves receiving first ultrasonic receiver signals from an ultrasonic receiver system corresponding to photoacoustic responses of the target object to the first light. In some examples, block 1110 may involve receiving, by the control system 106, signals from the receiver system 102 corresponding to ultrasonic waves generated by the target object responsive to the first light.

In this example, block 1115 involves causing the light source system to provide second light of a second wavelength to the target object at a second time. The second light may, for example, be emitted by at least a second light-emitting element of the light source system that is configured to emit light having a peak amplitude at the second wavelength. In some examples, block 1115 may involve controlling, by the control system 106, the light source system 104 to emit second light of the second wavelength to the target object at the second time.

According to this example, block 1120 involves receiving second ultrasonic receiver signals from the ultrasonic receiver system corresponding to photoacoustic responses of the target object to the second light. In some examples, block 1120 may involve receiving, by the control system 106, signals from the receiver system 102 corresponding to ultrasonic waves generated by the target object responsive to the second light.

In this example, block 1125 involves differentiating a desired signal from one or more background signals based, at least in part, on the first ultrasonic receiver signals and the second ultrasonic receiver signals. According to some examples, block 1125 may be performed by the control system 106. In some examples, the desired signal may correspond to a blood vessel within the target object. In some examples, method 1100 may involve estimating one or more blood vessel features based at least one of the first ultrasonic receiver signals or the second ultrasonic receiver signals. The one or more blood vessel features may, for example, include blood vessel diameter, blood vessel area, blood vessel profile, blood vessel distention, volumetric flow, pulse wave velocity, blood vessel wall thickness, or combinations thereof.

According to some examples, method 1100 may involve estimating blood pressure based, at least in part, on the one or more blood vessel features. In some examples, method 1100 may involve extracting and evaluating heart rate waveform (HRW) features, which may be based, at least in part, on the one or more blood vessel features.

Figure 12:
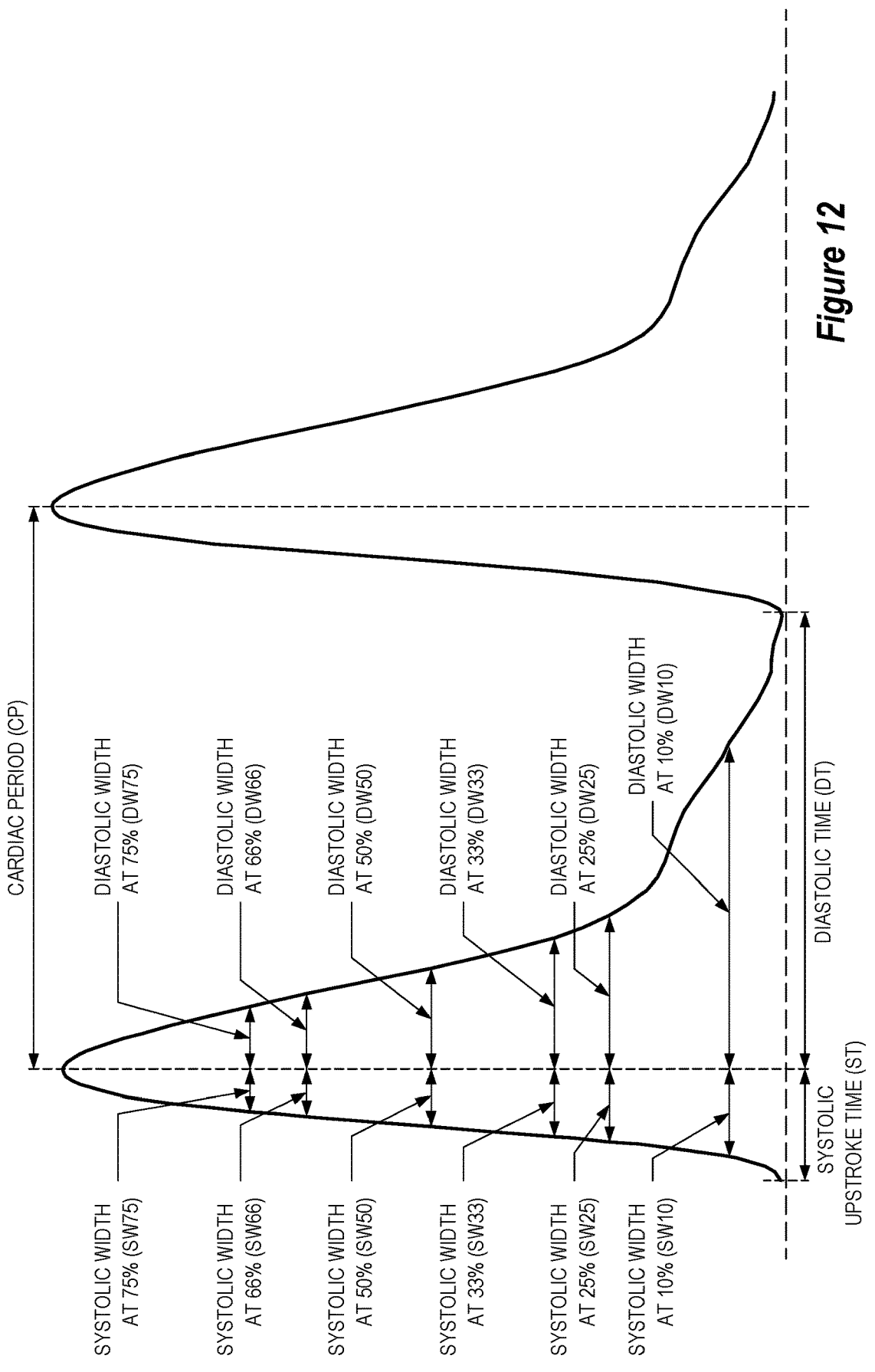
FIG. 12 shows examples of heart rate waveform (HRW) features that may be extracted according to some implementations of the method of FIG. 11.

FIG. 12 shows examples of heart rate waveform (HRW) features that may be extracted according to some implementations of the method of FIG. 11. The horizontal axis of FIG. 12 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 12 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/SW75, (DW66+SW66), DW66/SW66, (DW50+SW50), DW50/SW50, (DW33+SW33), DW33/SW33, (DW25+SW25), DW25/SW25 and/or (DW10+SW10), DW10/SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50/(DW10+SW10), etc.

Figure 13:
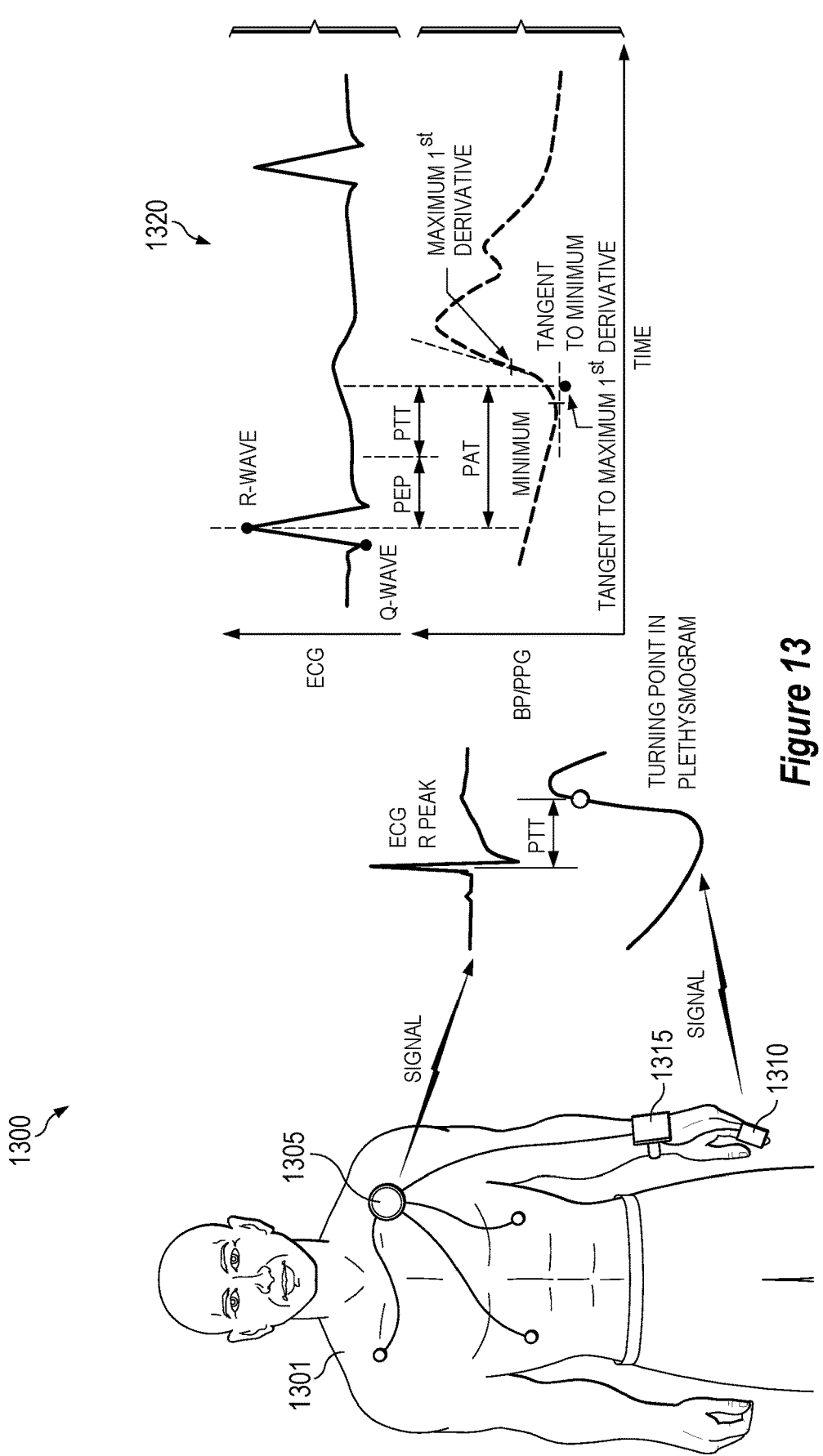
FIG. 13 shows examples of devices that may be used in a system for estimating blood pressure based, at least in part, on pulse transit time (PTT).

FIG. 13 shows examples of devices that may be used in a system for estimating blood pressure based, at least in part, on pulse transit time (PTT). As with other figures provided herein, the numbers, types and arrangements of elements are merely presented by way of example. According to this example, the system 1300 includes at least two sensors. In this example, the system 1300 includes at least an electrocardiogram sensor 1305 and a device 1310 that is configured to be mounted on a finger of the person 1301. In this example, the device 1310 is, or includes, an apparatus configured to perform at least some PAPG methods disclosed herein. For example, the device 1310 may be, or may include, the apparatus 300 of FIG. 1 or a similar apparatus.

As noted in the graph 1320, the PAT includes two components, the pre-ejection period (PEP, the time needed to convert the electrical signal into a mechanical pumping force and isovolumetric contraction to open the aortic valves) and the PTT. The starting time for the PAT can be estimated based on the QRS complex—an electrical signal characteristic of the electrical stimulation of the heart ventricles. As shown by the graph 1320, in this example the beginning of a pulse arrival time (PAT) may be calculated according to an R-Wave peak measured by the electrocardiogram sensor 1305 and the end of the PAT may be detected via analysis of signals provided by the device 1310. In this example, the end of the PAT is assumed to correspond with an intersection between a tangent to a local minimum value detected by the device 1310 and a tangent to a maximum slope/first derivative of the sensor signals after the time of the minimum value.

There are many known algorithms for blood pressure estimation based on the PTT and/or the PAT, some of which are summarized in Table 1 and described in the corresponding text on pages 5-10 of Sharma, M., et al., Cuff-Less and Continuous Blood Pressure Monitoring: a Methodological Review ("Sharma"), in Multidisciplinary Digital Publishing Institute (MDPI) Technologies 2017, 5, 21, both of which are hereby incorporated by reference.

Some previously-disclosed methods have involved calculating blood pressure according to one or more of the equations shown in Table 1 of Sharma, or other known equations, based on a PTT and/or PAT measured by a sensor system that includes a PPG sensor. As noted above, some disclosed PAPG-capable implementations are configured to distinguish artery HRWs from other HRWs. Such implementations may provide more accurate measurements of the PTT and/or PAT, relative to those measured by a PPG sensor. Therefore, disclosed PAPG-capable implementations may provide more accurate blood pressure estimations, even when the blood pressure estimations are based on previously-known formulae.

Other implementations of the system 1300 may not include the electrocardiogram sensor 1305. In some such implementations, the device 1315, which is configured to be mounted on a wrist of the person 1301, may be, or may include, an apparatus configured to perform at least some PAPG methods disclosed herein. For example, the device 1315 may be, or may include, the apparatus 200 of FIG. 2 or a similar apparatus. According to some such examples, the device 1315 may include a light source system and two or more ultrasonic receivers. One example is described below with reference to FIG. 15A. In some examples, the device 1315 may include an array of ultrasonic receivers.

In some implementations of the system 1300 that do not include the electrocardiogram sensor 1305, the device 1310 may include a light source system and two or more ultrasonic receivers. One example is described below with reference to FIG. 15B.

Figure 14:
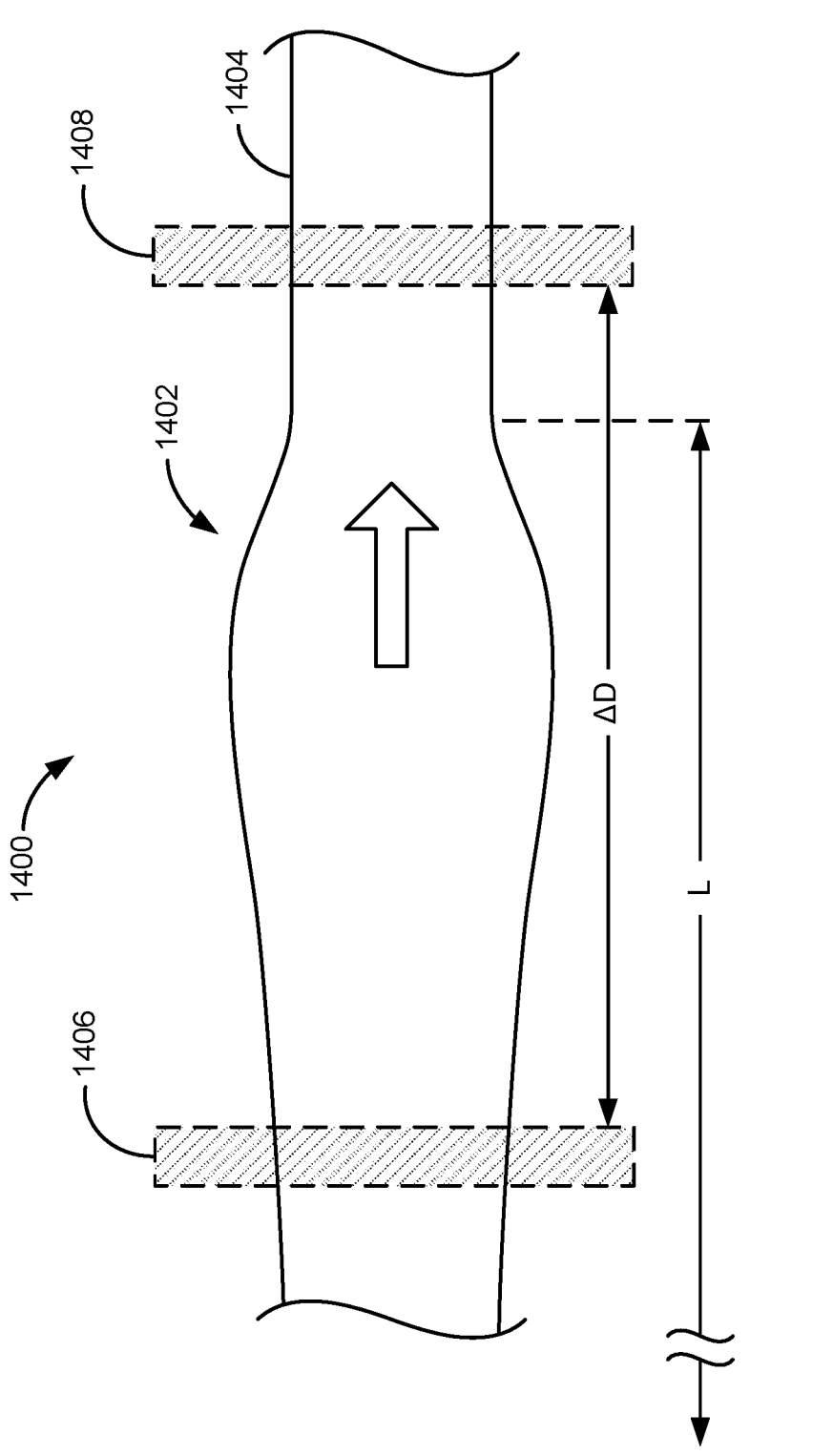
FIG. 14 shows a cross-sectional side view of a diagrammatic representation of a portion of an artery through which a pulse is propagating.

FIG. 14 shows a cross-sectional side view of a diagrammatic representation of a portion of an artery 1400 through which a pulse 1402 is propagating. The block arrow in FIG. 14 shows the direction of blood flow and pulse propagation. As diagrammatically shown, the propagating pulse 1402 causes strain in the arterial walls 1404, which is manifested in the form of an enlargement in the diameter (and consequently the cross-sectional area) of the arterial walls-referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the pulse wave velocity (PWV) of a propagating pulse may be estimated by measuring the pulse transit time (PTT) of the pulse as it propagates from a first physical location along an artery to another more distal second physical location along the artery. It will be appreciated that this PTT is different from the PTT that is described above with reference to FIG. 15. However, either version of the PTT may be used for the purpose of blood pressure estimation. Assuming that the physical distance ΔD between the first and the second physical locations is ascertainable, the PWV can be estimated as the quotient of the physical spatial distance ΔD traveled by the pulse divided by the time (PTT) the pulse takes in traversing the physical spatial distance ΔD. Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. In such examples, the PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance ΔD through which the pulse propagates between the first physical location and the second physical location. More specifically, the PWV generally depends on a number of factors including the density of the blood ρ, the stiffness E of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length ΔD between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or more generally as "sensor data") associated with an arterial distension signal obtained by each of a first arterial distension sensor 1406 and a second arterial distension sensor 1408 proximate first and second physical locations, respectively, along an artery of interest.

In some particular implementations, the first arterial distension sensor 1406 and the second arterial distension sensor 1408 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure P estimated based on the PWV is more representative of the true blood pressure. In some implementations, the magnitude of the distance ΔD of separation between the first arterial distension sensor 1406 and the second arterial distension sensor 1408 (and consequently the distance between the first and the second locations along the artery) can be in the range of about 1 centimeter (cm) to tens of centimeters-long enough to distinguish the arrival of the pulse at the first physical location from the arrival of the pulse at the second physical location, but close enough to provide sufficient assurance of arterial consistency. In some specific implementations, the distance ΔD between the first and the second arterial distension sensors 1406 and 1408 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance ΔD between the first and the second arterial distension sensors 1406 and 1408 can be less than or equal to 1 cm, for example, about 0.1 cm, about 0.25 cm, about 0.5 cm or about 0.75 cm. By way of reference, a typical PWV can be about 15 meters per second (m/s). Using an ambulatory monitoring device in which the first and the second arterial distension sensors 1406 and 1408 are separated by a distance of about 5 cm, and assuming a PWV of about 15 m/s implies a PTT of approximately 3.3 milliseconds (ms).

The value of the magnitude of the distance ΔD between the first and the second arterial distension sensors 1406 and 1408, respectively, can be preprogrammed into a memory within a monitoring device that incorporates the sensors (for example, such as a memory of, or a memory configured for communication with, the control system 306 that is described above with reference to FIG. 1). As will be appreciated by a person of ordinary skill in the art, the spatial length L of a pulse can be greater than the distance ΔD from the first arterial distension sensor 1406 to the second arterial distension sensor 1408 in such implementations. As such, although the diagrammatic pulse 1402 shown in FIG. 14 is shown as having a spatial length L comparable to the distance between the first arterial distension sensor 1406 and the second arterial distension sensor 1408, in actuality each pulse can typically have a spatial length L that is greater and even much greater than (for example, about an order of magnitude or more than) the distance ΔD between the first and the second arterial distension sensors 1406 and 1408.

Sensing Architecture and Topology

In some implementations of the ambulatory monitoring devices disclosed herein, both the first arterial distension sensor 1406 and the second arterial distension sensor 1408 are sensors of the same sensor type. In some such implementations, the first arterial distension sensor 1406 and the second arterial distension sensor 1408 are identical sensors. In such implementations, each of the first arterial distension sensor 1406 and the second arterial distension sensor 1408 utilizes the same sensor technology with the same sensitivity to the arterial distension signal caused by the propagating pulses, and has the same time delays and sampling characteristics. In some implementations, each of the first arterial distension sensor 1406 and the second arterial distension sensor 1408 is configured for photoacoustic plethysmography (PAPG) sensing, e.g., as disclosed elsewhere herein. Some such implementations include a light source system and two or more ultrasonic receivers, which may be instances of the light source system 104 and the receiver system 102 of FIG. 1. In some implementations, each of the first arterial distension sensor 1406 and the second arterial distension sensor 1408 is configured for ultrasound sensing via the transmission of ultrasonic signals and the receipt of corresponding reflections. In some alternative implementations, each of the first arterial distension sensor 1406 and the second arterial distension sensor 1408 may be configured for impedance plethysmography (IPG) sensing, also referred to in biomedical contexts as bioimpedance sensing. In various implementations, whatever types of sensors are utilized, each of the first and the second arterial distension sensors 1406 and 1408 broadly functions to capture and provide arterial distension data indicative of an arterial distension signal resulting from the propagation of pulses through a portion of the artery proximate to which the respective sensor is positioned. For example, the arterial distension data can be provided from the sensor to a processor in the form of voltage signal generated or received by the sensor based on an ultrasonic signal or an impedance signal sensed by the respective sensor.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

A bioimpedance sensor generally functions by applying an electrical excitation signal at an excitation carrier frequency to a region of interest via two or more input electrodes, and detecting an output signal (or output signals) via two or more output electrodes. In some more specific implementations, the electrical excitation signal is an electrical current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance (or inversely the admittance) of the underlying arteries, which fluctuates synchronously with the user's heartbeat as described above. To determine various biological characteristics, information in the detected voltage response signal is generally demodulated from the excitation carrier frequency component using various analog or digital signal processing circuits, which can include both passive and active components.

In some examples incorporating ultrasound sensors, measurements of arterial distension may involve directing ultrasonic waves into a limb towards an artery, for example, via one or more ultrasound transducers. Such ultrasound sensors also are configured to receive reflected waves that are based, at least in part, on the directed waves. The reflected waves may include scattered waves, specularly reflected waves, or both scattered waves and specularly reflected waves. The reflected waves provide information about the arterial walls, and thus the arterial distension.

In some implementations, regardless of the type of sensors utilized for the first arterial distension sensor 1406 and the second arterial distension sensor 1408, both the first arterial distension sensor 1406 and the second arterial distension sensor 1408 can be arranged, assembled or otherwise included within a single housing of a single ambulatory monitoring device. As described above, the housing and other components of the monitoring device can be configured such that when the monitoring device is affixed or otherwise physically coupled to a subject, both the first arterial distension sensor 1406 and the second arterial distension sensor 1408 are in contact with or in close proximity to the skin of the user at first and second locations, respectively, separated by a distance $\Delta D$, and in some implementations, along a stretch of the artery between which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the wearable monitoring devices described herein are non-invasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 15A:
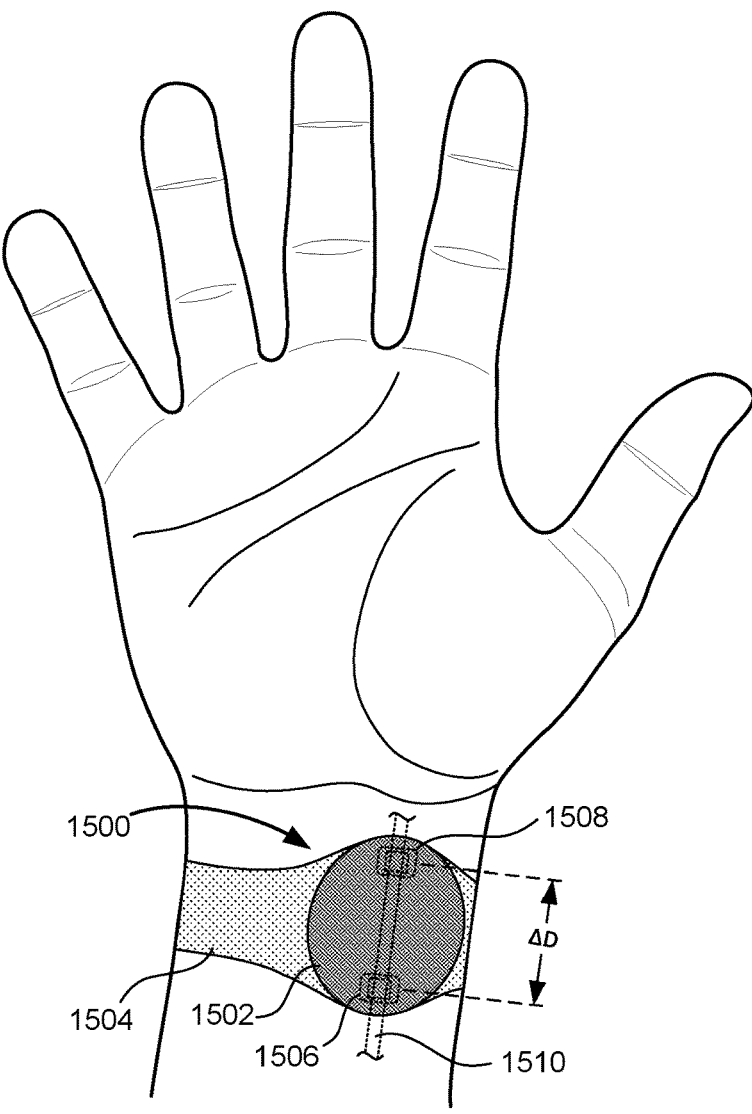
FIG. 15A shows an example ambulatory monitoring device designed to be worn around a wrist according to some implementations.

In some implementations, the ambulatory monitoring device can be positioned around a wrist of a user with a strap or band, similar to a watch or fitness/activity tracker. FIG. 15A shows an example ambulatory monitoring device 1500 designed to be worn around a wrist according to some implementations. In the illustrated example, the monitoring device 1500 includes a housing 1502 integrally formed with, coupled with or otherwise integrated with a wristband 1504. The first and the second arterial distension sensors 1506 and 1508 may, in some instances, each include an instance of the ultrasonic receiver system 102 and a portion of the light source system 104 that are described above with reference to FIG. 1. In this example, the ambulatory monitoring device 1500 is coupled around the wrist such that the first and the second arterial distension sensors 1506 and 1508 within the housing 1502 are each positioned along a segment of the radial artery 1510 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial distension sensors 1506 and 1508 are separated by a fixed distance ΔD. In some other implementations, the ambulatory monitoring device 1500 can similarly be designed or adapted for positioning around a forearm, an upper arm, an ankle, a lower leg, an upper leg, or a finger (all of which are hereinafter referred to as "limbs") using a strap or band.

Figure 15B:
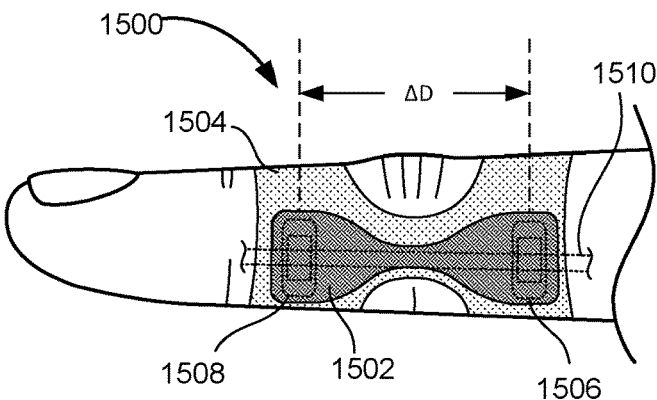
FIG. 15B shows an example ambulatory monitoring device 1500 designed to be worn on a finger according to some implementations.

FIG. 15B shows an example ambulatory monitoring device 1500 designed to be worn on a finger according to some implementations. The first and the second arterial distension sensors 1506 and 1508 may, in some instances, each include an instance of the ultrasonic receiver 102 and a portion of the light source system 104 that are described above with reference to FIG. 1.

In some other implementations, the ambulatory monitoring devices disclosed herein can be positioned on a region of interest of the user without the use of a strap or band. For example, the first and the second arterial distension sensors 1506 and 1508 and other components of the monitoring device can be enclosed in a housing that is secured to the skin of a region of interest of the user using an adhesive or other suitable attachment mechanism (an example of a "patch" monitoring device).

Figure 15C:
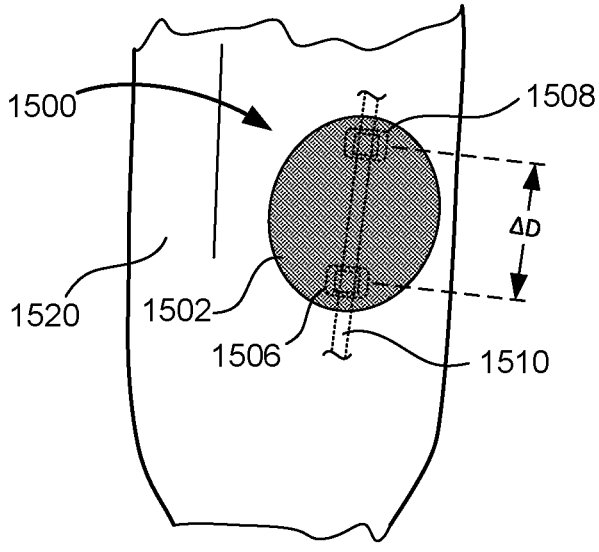
FIG. 15C shows an example ambulatory monitoring device 1500 designed to reside on an earbud according to some implementations.

FIG. 15C shows an example ambulatory monitoring device 1500 designed to reside on an earbud according to some implementations. According to this example, the ambulatory monitoring device 1500 is coupled to the housing of an earbud 1520. The first and second arterial distension sensors 1506 and 1508 may, in some instances, each include an instance of the ultrasonic receiver 102 and a portion of the light source system 104 that are described above with reference to FIG. 1.

Implementation examples are described in the following numbered clauses:

1A. An apparatus, including: a platen; a light source system configured for providing light to a target object on an outer surface of the platen, the light including at least first light of a first wavelength and second light of a second wavelength; an ultrasonic receiver system configured to receive ultrasonic waves generated by the target object responsive to the light from the light source system; and a control system configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and differentiate a desired signal from one or more background signals based, at least in part, on the first ultrasonic receiver signals and the second ultrasonic receiver signals.

2A. The apparatus of clause 1A, where the desired signal corresponds to a blood vessel within the target object.

3A. The apparatus of clause 2A, where the control system is further configured to estimate one or more blood vessel features based on at least one of the first ultrasonic receiver signals or the second ultrasonic receiver signals.

4A. The apparatus of clause 3A, where the one or more blood vessel features include blood vessel diameter, blood vessel area, blood vessel profile, blood vessel distention, volumetric flow, pulse wave velocity, blood vessel wall thickness, or combinations thereof.

5A. The apparatus of clause 3A or clause 4A, where the control system is further configured to estimate blood pressure based, at least in part, on the one or more blood vessel features.

6A. The apparatus of any one of clauses 1A-5A, where the light source system includes a first laser configured to emit the first light and a second laser configured to emit the second light.

7A. The apparatus of any one of clauses 1A-6A, where the light source system further includes a light guide system configured to convey light from the light source system to the platen.

8A. The apparatus of clause 7A, where a first light guide portion of the light guide system resides between at least two ultrasonic receiver system portions.

9A. The apparatus of clause 8A, where the light guide system includes a second light guide portion configured to convey the first light to the first light guide portion and a third light guide portion configured to convey the second light to the first light guide portion.

10A. The apparatus of clause 7A, where at least a portion of the ultrasonic receiver system is arranged in a ring around a first light guide portion.

11A. The apparatus of clause 7A, where the light guide system includes a light guide configured to convey light in a direction that is parallel to, or substantially parallel to, the platen.

12A. The apparatus of clause 11A, where the light guide system includes a plurality of light extracting elements residing within the light guide, the light extracting elements being configured to direct light towards the platen.

13A. The apparatus of any one of clauses 7A-12A, where the ultrasonic receiver system includes an array of ultrasonic receiver elements.

14A. The apparatus of clause 13A, where the array of ultrasonic receiver elements includes a linear array of ultrasonic receiver elements.

15A. The apparatus of clause 13A, where the array of ultrasonic receiver elements includes a two-dimensional array of ultrasonic receiver elements.

16A. The apparatus of any one of clauses 13A-15A, where the array of ultrasonic receiver elements is transparent.

17A. The apparatus of any one of clauses 1A-16A, where the ultrasonic receiver system includes a transparent piezoelectric layer.

18A. The apparatus of any one of clauses 1A-17A, where the ultrasonic receiver system includes a transparent electrode layer.

19A. The apparatus of any one of clauses 1A-18A, where the light source system is configured for providing the first light to the target object along a first axis and is configured for providing the second light to the target object along the first axis.

20A. The apparatus of clause 19A, where the ultrasonic receiver system receives acoustic waves from the target object along a second axis that is different from the first axis, the acoustic waves corresponding to the first ultrasonic receiver signals and the second ultrasonic receiver signals.

21A. The apparatus of clause 20A, where the second axis is separated from the first axis by an angle in a range from 10 degrees to 60 degrees.

22A. A method, including: causing a light source system to provide first light of a first wavelength to a target object at a first time; receiving first ultrasonic receiver signals from an ultrasonic receiver system corresponding to photoacoustic responses of the target object to the first light; causing the light source system to provide second light of a second wavelength to the target object at a second time; receiving second ultrasonic receiver signals from the ultrasonic receiver system corresponding to photoacoustic responses of the target object to the second light; and differentiating a desired signal from one or more background signals based, at least in part, on the first ultrasonic receiver signals and the second ultrasonic receiver signals.

23A. The method of clause 22A, where the desired signal corresponds to a blood vessel within the target object.

24A. The method of clause 23, further including estimating one or more blood vessel features based at least one of the first ultrasonic receiver signals or the second ultrasonic receiver signals.

25A. The method of clause 24A, where the one or more blood vessel features include blood vessel diameter, blood vessel area, blood vessel profile, blood vessel distention, volumetric flow, pulse wave velocity, blood vessel wall thickness, or combinations thereof.

26A. The method of clause 24A or clause 25A, further including estimating blood pressure based, at least in part, on the one or more blood vessel features.

27A. One or more non-transitory computer-readable media having instructions for performing a method stored thereon, the method including: causing a light source system to provide first light of a first wavelength to a target object at a first time; receiving first ultrasonic receiver signals from an ultrasonic receiver system corresponding to photoacoustic responses of the target object to the first light; causing the light source system to provide second light of a second wavelength to the target object at a second time; receiving second ultrasonic receiver signals from the ultrasonic receiver system corresponding to photoacoustic responses of the target object to the second light; and differentiating a desired signal from one or more background signals based, at least in part, on the first ultrasonic receiver signals and the second ultrasonic receiver signals.

28A. The one or more non-transitory computer-readable media of clause 27A, where the desired signal corresponds to a blood vessel within the target object and where the method further includes estimating one or more blood vessel features based at least one of the first ultrasonic receiver signals or the second ultrasonic receiver signals.

29A. The one or more non-transitory computer-readable media of clause 28A, where the one or more blood vessel features include blood vessel diameter, blood vessel area, blood vessel profile, blood vessel distention, volumetric flow, pulse wave velocity, blood vessel wall thickness, or combinations thereof.

30A. The one or more non-transitory computer-readable media of clause 28A or clause 29A, where the method further includes estimating blood pressure based, at least in part, on the one or more blood vessel features.

1B. An apparatus, including: a platen; a light source system configured for providing light to a target object on an outer surface of the platen, the light including at least first light of a first wavelength emitted by a first light-emitting device and second light of a second wavelength emitted by a second light-emitting device, the light source system being configured for providing the first light to the target object along a first axis and being configured for providing the second light to the target object along the first axis; an ultrasonic receiver system configured to receive ultrasonic waves generated by the target object responsive to the light from the light source system; and a control system configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and estimate one or more blood vessel features based on at least one of the first ultrasonic receiver signals or the second ultrasonic receiver signals.

2B. The apparatus of clause 1B, where the control system is further configured to differentiate a desired signal from one or more background signals based, at least in part, on the first ultrasonic receiver signals and the second ultrasonic receiver signals.

3B. The apparatus of clause 2B, where the desired signal corresponds to a blood vessel within the target object.

4B. The apparatus of any one of clauses 1B-3B, where the one or more blood vessel features include blood vessel diameter, blood vessel area, blood vessel profile, blood vessel distention, volumetric flow, pulse wave velocity, blood vessel wall thickness, or combinations thereof.

5B. The apparatus of any one of clauses 1B-4B, where the control system is further configured to estimate blood pressure based, at least in part, on the one or more blood vessel features.

6B. The apparatus of any one of clauses 1B-5B, where the first light-emitting device includes a first laser configured to emit the first light and where the second light-emitting device includes a second laser configured to emit the second light.

7B. The apparatus of any one of clauses 1B-6B, where the light source system further includes a light guide system configured to convey light from the light source system to the platen.

8B. The apparatus of clause 7B, where a first light guide portion of the light guide system resides between at least two ultrasonic receiver system portions.

9B. The apparatus of clause 8B, where the light guide system includes a second light guide portion configured to convey the first light to the first light guide portion and a third light guide portion configured to convey the second light to the first light guide portion.

10B. The apparatus of any one of clauses 7B-9B, where at least a portion of the ultrasonic receiver system is arranged in a ring around a first light guide portion.

11B. The apparatus of any one of clauses 7B-10B, where the light guide system includes a first light-directing device and a second light-directing device, the second light-directing device being configured to reflect light emitted by the second light-emitting device towards the first light-directing device.

12B. The apparatus of clause 11B, where the first light-directing device is configured to direct light emitted by the first light-emitting device and the second light-emitting device along the first axis.

13B. The apparatus of clause 12B, where the first axis is orthogonal, or substantially orthogonal, to a plane of the platen.

14B. The apparatus of any one of clauses 11B-13B, where the first light-directing device includes a mirror and the second light-directing device includes a beamsplitter.

15B. The apparatus of any one of clauses 1B-14B, where the first axis is offset by an angle in a range of 10 degrees to 60 degrees of a normal to a plane of the platen a linear array of ultrasonic receiver elements.

16B. The apparatus of clause 15B, where the plane corresponds to an outer surface of the platen.

17B. The apparatus of any one of clauses 1B-16B, where the ultrasonic receiver system includes a linear array of ultrasonic receiver elements, a two-dimensional array of ultrasonic receiver elements, or both.

18B. The apparatus of any one of clauses 1B-17B, where the ultrasonic receiver system includes an array of transparent ultrasonic receiver elements transparent piezoelectric layer, a transparent electrode layer, or combinations thereof.

19B. The apparatus of any one of clauses 1B-18B, where the ultrasonic receiver system receives acoustic waves from the target object along a second axis that is different from the first axis, the acoustic waves corresponding to the first ultrasonic receiver signals and the second ultrasonic receiver signals.

20B. The apparatus of clause 19B, where the second axis is separated from the first axis by an angle in a range from 10 degrees to 60 degrees.

1C. An apparatus, including: a platen; a light source system configured for providing light to a target object on an outer surface of the platen, the light including at least first light of a first wavelength emitted by a first light-emitting device and second light of a second wavelength emitted by a second light-emitting device, the light source system including a light guide system configured to convey the first light and the second light to the platen; an ultrasonic receiver system configured to receive ultrasonic waves generated by the target object responsive to the light from the light source system; and a control system configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and estimate one or more blood vessel features based on at least one of the first ultrasonic receiver signals or the second ultrasonic receiver signals.

2C. The apparatus of clause 1C, where the control system is further configured to differentiate a desired signal from one or more background signals based, at least in part, on the first ultrasonic receiver signals and the second ultrasonic receiver signals.

3C. The apparatus of clause 2C, where the desired signal corresponds to a blood vessel within the target object.

4C. The apparatus of any one of clauses 1C-3C, where the one or more blood vessel features include blood vessel diameter, blood vessel area, blood vessel profile, blood vessel distention, volumetric flow, pulse wave velocity, blood vessel wall thickness, or combinations thereof.

5C. The apparatus of any one of clauses 1C-4C, where the control system is further configured to estimate blood pressure based, at least in part, on the one or more blood vessel features.

6C. The apparatus of any one of clauses 1C-5C, where the first light-emitting device includes a first laser configured to emit the first light and the second light-emitting device includes a second laser configured to emit the second light.

7C. The apparatus of any one of clauses 1C-6C, where a first light guide portion of the light guide system resides between at least two ultrasonic receiver system portions.

8C. The apparatus of clause 7C, where the light guide system includes a second light guide portion configured to convey the first light to the first light guide portion and a third light guide portion configured to convey the second light to the first light guide portion.

9C. The apparatus of any one of clauses 1C-8C, where at least a portion of the ultrasonic receiver system is arranged in a ring around a first light guide portion.

10C. The apparatus of any one of clauses 1C-9C, where the light guide system includes a light guide configured to convey light in a direction that is parallel to, or substantially parallel to, the platen.

11C. The apparatus of clause 10C, where the light guide system includes a plurality of light extracting elements residing within the light guide, the light extracting elements being configured to direct light towards the platen.

12C. The apparatus of any one of clauses 1C-11C, where the ultrasonic receiver system includes a linear array of ultrasonic receiver elements, a two-dimensional array of ultrasonic receiver elements, or both.

13C. The apparatus of any one of clauses 1C-12C, where the ultrasonic receiver system includes an array of transparent ultrasonic receiver elements, a transparent piezoelectric layer, a transparent electrode layer, or combinations thereof.

14C. The apparatus of any one of clauses 1C-13C, where the light source system is configured for providing the first light to the target object along a first axis and is configured for providing the second light to the target object along the first axis.

15C. The apparatus of clause 14C, where the ultrasonic receiver system receives acoustic waves from the target object along a second axis that is different from the first axis, the acoustic waves corresponding to the first ultrasonic receiver signals and the second ultrasonic receiver signals.

16C. The apparatus of clause 15C, where the second axis is separated from the first axis by an angle in a range from 10 degrees to 60 degrees.

1D. An apparatus, including: a platen; a light source system configured for providing light to a target object on an outer surface of the platen, the light including at least first light of a first wavelength emitted by a first light-emitting device and second light of a second wavelength emitted by a second light-emitting device, the light source system including a light guide system including one or more light guides configured to convey light in a direction that is parallel to, or substantially parallel to, an outer surface of the platen; an ultrasonic receiver system configured to receive ultrasonic waves generated by the target object responsive to the light from the light source system; and a control system configured to: cause the light source system to provide the first light to the target object at a first time; receive first ultrasonic receiver signals from the ultrasonic receiver system corresponding to photoacoustic responses of the target object to the first light; cause the light source system to provide the second light to the target object at a second time; receive second ultrasonic receiver signals from the ultrasonic receiver system corresponding to photoacoustic responses of the target object to the second light; and estimate one or more blood vessel features based on at least one of the first ultrasonic receiver signals or the second ultrasonic receiver signals.

2D. The apparatus of clause 1D, where the control system is further configured to differentiate a desired signal from one or more background signals based, at least in part, on the first ultrasonic receiver signals and the second ultrasonic receiver signals.

3D. The apparatus of clause 2D, where the desired signal corresponds to a blood vessel within the target object.

4D. The apparatus of any one of clauses 1D-3D, where the one or more blood vessel features include blood vessel diameter, blood vessel area, blood vessel profile, blood vessel distention, volumetric flow, pulse wave velocity, blood vessel wall thickness, or combinations thereof.

5D. The apparatus of any one of clauses 1D-4D, where the control system is further configured to estimate blood pressure based, at least in part, on the one or more blood vessel features.

6D. The apparatus of any one of clauses 1D-5D, where the first light-emitting device includes a first laser configured to emit the first light and the second light-emitting device includes a second laser configured to emit the second light.

7D. The apparatus of any one of clauses 1D-6D, where the light guide system includes a plurality of light extracting elements residing within the one or more light guides, the light extracting elements being configured to direct light towards the platen.

8D. The apparatus of clause 7D, where the light extracting elements include one or more indentations in, protuberances of, or structures formed on, a light guide surface.

9D. The apparatus of clause 7D or clause 8D, where the light extracting elements include one or more three-dimensional shapes formed from the indentations in, protuberances of, or structures formed on, the light guide surface.

10D. The apparatus of any one of clauses 7D-9D, where the light extracting elements include one or more beam splitters.

11D. The apparatus of any one of clauses 7D-10D, where the light extracting elements include one or more mirrors or other reflective structures.

12D. The apparatus of any one of clauses 7D-11D, where a two-dimensional array of light-extracting elements is configured to provide substantially uniform light to an illuminated area of an outer surface of the platen.

13D. The apparatus of any one of clauses 7D-12D, where at least some light-extracting elements are arranged with unequal spacing within the one or more light guides.

14D. The apparatus of clause 13D, where light-extracting elements located farther from the first light-emitting device are spaced closer together than light-extracting elements located closer to the first light-emitting device.

15D. The apparatus of any one of clauses 1D-14D, where the ultrasonic receiver system includes a linear array of ultrasonic receiver elements, a two-dimensional array of ultrasonic receiver elements, or both.

16D. The apparatus of any one of clauses 1D-15D, where the ultrasonic receiver system includes an array of transparent ultrasonic receiver elements, a transparent piezoelectric layer, a transparent electrode layer, or combinations thereof.

17D. The apparatus of clause 16D, further including a transparent backing layer residing between the one or more light guides and the array of transparent ultrasonic receiver elements, the transparent piezoelectric layer, the transparent electrode layer, or combinations thereof.

18D. The apparatus of any one of clauses 1D-17D, where one or more ultrasonic receiver elements of the ultrasonic receiver system resides on a first side of the one or more light guides and receiver system circuitry resides on a second and opposing side of the one or more light guides.

19D. The apparatus of any one of clauses 1D-18D, where the first light-emitting device resides on a first side of the platen and the second light-emitting device resides on a second side of the platen.

20D. The apparatus of clause 19D, where the first side is adjacent to the second side.

21D. The apparatus of any one of clauses 1D-20D, where the first light-emitting device and the second light-emitting device reside on a first side of the platen.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. An apparatus, comprising:

a platen;

a light source system configured for providing light to a target object on an outer surface of the platen, the light including at least first light of a first wavelength emitted by a first light-emitting device and second light of a second wavelength emitted by a second light-emitting device, the light source system including a light guide system configured to convey the first light and the second light to the platen;

an ultrasonic receiver system configured to receive ultrasonic waves generated by the target object responsive to the light from the light source system; and a control system configured to:

cause the light source system to provide the first light to the target object at a first time;

receive first ultrasonic receiver signals from the ultrasonic receiver system corresponding to photoacoustic responses of the target object to the first light;

cause the light source system to provide the second light to the target object at a second time;

receive second ultrasonic receiver signals from the ultrasonic receiver system corresponding to photoacoustic responses of the target object to the second light;

differentiate a desired signal from one or more background signals based, at least in part, on one or more amplitude differences between the first ultrasonic receiver signals and the second ultrasonic receiver signals; and estimate one or more blood vessel features based on at least one of the first ultrasonic receiver signals or the second ultrasonic receiver signals.

2. The apparatus of claim 1, wherein the one or more background signals correspond to electromagnetic interference or skin.

3. The apparatus of claim 1, wherein the desired signal corresponds to a blood vessel within the target object.

4. The apparatus of claim 1, wherein the one or more blood vessel features include blood vessel diameter, blood vessel area, blood vessel profile, blood vessel distention, volumetric flow, pulse wave velocity, blood vessel wall thickness, or combinations thereof.

5. The apparatus of claim 1, wherein the control system is further configured to estimate blood pressure based, at least in part, on the one or more blood vessel features.

6. The apparatus of claim 1, wherein the first light-emitting device comprises a first laser configured to emit the first light and the second light-emitting device comprises a second laser configured to emit the second light.

7. The apparatus of claim 1, wherein a first light guide portion of the light guide system resides between at least two ultrasonic receiver system portions.

8. The apparatus of claim 7, wherein the light guide system includes a second light guide portion configured to convey the first light to the first light guide portion and a third light guide portion configured to convey the second light to the first light guide portion.

9. The apparatus of claim 1, wherein at least a portion of the ultrasonic receiver system is arranged in a ring around a first light guide portion.

10. The apparatus of claim 1, wherein the light guide system includes a light guide configured to convey light in a direction that is parallel to, or substantially parallel to, the platen, wherein "substantially parallel to" means within 20 degrees of being parallel.

11. The apparatus of claim 10, wherein the light guide system includes a plurality of light extracting elements residing within the light guide, the light extracting elements being configured to direct light towards the platen.

12. The apparatus of claim 1, wherein the ultrasonic receiver system includes a linear array of ultrasonic receiver elements, a two-dimensional array of ultrasonic receiver elements, or both.

13. The apparatus of claim 1, wherein the ultrasonic receiver system includes an array of transparent ultrasonic receiver elements, a transparent piezoelectric layer, a transparent electrode layer, or combinations thereof.

14. The apparatus of claim 1, wherein the light source system is configured for providing the first light to the target object along a first axis and is configured for providing the second light to the target object along the first axis.

15. The apparatus of claim 14, wherein the ultrasonic receiver system receives acoustic waves from the target object along a second axis that is different from the first axis, the acoustic waves corresponding to the first ultrasonic receiver signals and the second ultrasonic receiver signals.

16. The apparatus of claim 15, wherein the second axis is separated from the first axis by an angle in a range from 10 degrees to 60 degrees.

* * * * *